', '

(12) United States Patent
Cooke et al.

(10) Patent No.: US 7,595,148 B2
(45) Date of Patent: Sep. 29, 2009

(54) METHODS AND COMPOSITIONS FOR MODULATING T LYMPHOCYTES

(75) Inventors: Michael P. Cooke, Del Mar, CA (US); Karsten Sauer, San Diego, CA (US); Tim Wiltshire, Encinitas, CA (US); Lisa Tarantino, Encinitas, CA (US); Colin Fletcher, Del Mar, CA (US); Ben Wen, Encinitas, CA (US)

(73) Assignee: IRM LLC, Hamilton (BM)

( * ) Notice: Subject to any disclaimer, the term of this patent is extended or adjusted under 35 U.S.C. 154(b) by 308 days.

(21) Appl. No.: 10/764,330

(22) Filed: Jan. 23, 2004

(65) Prior Publication Data

US 2004/0265790 A1 Dec. 30, 2004

Related U.S. Application Data

(60) Provisional application No. 60/442,792, filed on Jan. 25, 2003.

(51) Int. Cl.
*C12Q 1/00* (2006.01)
*C12Q 1/68* (2006.01)
*C12N 5/00* (2006.01)
*C12N 5/02* (2006.01)

(52) U.S. Cl. ............................ 435/4; 435/6; 435/375

(58) Field of Classification Search ............ None
See application file for complete search history.

(56) References Cited

U.S. PATENT DOCUMENTS 5,583,033 A 12/1996 Terstappen
5,677,139 A 10/1997 Johnason

OTHER PUBLICATIONS

Vanweyenberg et al., 1995, J. Biochem. vol. 306: 429-435.*
Wen et al., 2004, PNAS vol. 101: 5604-5609.*
Pouillon et al. 2003, Nat. Immunol. vol. 4: 1136-1143.*
da Silva et al., 1994, J. Biol. Chem. vol. 269: 12521-12526.*
MedlinePlus Medical Dictionary definition for "animal", 2005, pp. 1-2.*
Janeway and Travers, Immunobiology, 1997, pp. 6:6-6:7.*
Chang YT, et al. Related Articles, Links Purine-based inhibitors of inositol-1,4,5-trisphosphate-3-kinase. Chembiochem. Sep. 2, 2002;3(9):897-901.
Irvine, Robin. Inositol phosphates: Does IP4 run a protection racket? Current Biology 2001. vol. 11, No. 5, p. 172-174.
Irvine, Robin, et al. Back In The Water: The Return Of The Inositol Phosphates. Nature Reviews, Molecular Cell Biology. May 2001, vol. 2, p. 327-338.
Jun, Kisun et al. Enhanced Hippocampal CA1 LTP but Normal Spatial Learning in Inositol 1,4,5-trisphosphate 3-kinase (A)-Deficient Mice. Learning & Memory, 1998, vol. 5, p. 317-330.
Woodring, Pamela J. et al. Expression, Purification, and Regulation of Two Isoforms of the Inositol 1,4,5-Trisphosphate 3-Kinase. The Journal of Biological Chemistry, 1997, vol. 272, No. 48, p. 30447-30454.
Dewaste, Valerie, et al. Cloning and expression of a cDNA encoding human inositol 1,4,5-trisphosphate 3-kinase C. Biochem, 2000, p. 343-351.

* cited by examiner

*Primary Examiner*—G. R Ewoldt
*Assistant Examiner*—Amy E Juedes
(74) *Attorney, Agent, or Firm*—Emily Tongco Wu; Genomics Institute of the Novartis Research Foundation

(57) ABSTRACT

This invention provides novel methods and compositions for modulating T cell differentiation and T cell responses. The modulators are identified by screening test compounds for ability to modulate an inositol 1,4,5-trisphosphate 3-kinase (IP3K). The IP3K modulators can be further examined for their activity in modulating development of progenitor T cells (e.g., $CD4^+/CD8^+$ double positive T cells) into mature $CD4^+$ or $CD8^+$ single positive T cells. Pharmaceutical compositions comprising these T cell modulators can be administered to a subject to modulate T cell immune responses, to suppress inflammations, and to treat disease conditions such as autoimmune diseases, graft rejection or allergies.

11 Claims, 3 Drawing Sheets

METHODS AND COMPOSITIONS FOR MODULATING T LYMPHOCYTES

CROSS-REFERENCE TO RELATED APPLICATIONS

This application claims the benefit of priority to U.S. Provisional Patent Application Ser. No. 60/442,792 (filed Jan. 25, 2003), the disclosure of which is incorporated herein by reference in its entirety and for all purposes.

FIELD OF THE INVENTION

The present invention generally relates to novel modulators of IP3K kinases and therapeutic applications of such modulators. More particularly, the invention pertains to novel IP3K modulators that modulate T lymphocyte differentiation and function, and to methods of using such modulators to treat diseases and conditions mediated by abnormal T cell activities.

BACKGROUND OF THE INVENTION

In the development of the immune system, T lymphocytes are derived from precursor stem cells which enter the thymus to undergo differentiation and maturation. T lymphocyte differentiation normally occurs via a series of discrete developmental stages involving an initial primitive progenitor cell without lymphocyte specific cell surface markers ($CD34^+$ $CD3^-$ $CD4^-$ $CD8^-$), followed by acquisition of lymphocyte specific markers and loss of CD34 ($CD34^-$ $CD3^+$ $CD4^+$ $CD8^+$), followed by differentiation into mature $CD3^+$ T cells expressing either CD4 or CD8 ($CD3^+$ $CD4^+$ $CD8^-$ or $CD3^+$ $CD4^-$ $CD8^+$).

While normal T cells are an integral part of mammalian immune responses, in some instances it is desirable to inhibit undesirable immune responses such as undesirable proliferation of T cells. For instance, autoimmune diseases are characterized as an immune reaction against "self" antigens. Autoimmune diseases include systemic lupus erythematosus (SLE), rheumatoid arthritis (RA) and multiple sclerosis (MS). T cell responses have also been implicated in graft rejection and graft versus host disease (GVHD). Thus, treatment directed to inhibition of T cell differentiation would be greatly desired to treat such undesired immune responses.

There is a need for new compounds and methods for inhibiting T cell immune responses and for treating the above-noted diseases and conditions. By providing novel methods and compositions for modulating T cell development and functions, the instant invention fulfills this and other needs.

SUMMARY OF THE INVENTION

In one aspect, the present invention provides methods for identifying agents that modulate T lymphocyte development or function. The methods entail assaying a cellular activity of an inositol 1,4,5-trisphosphate 3-kinase (IP3K) or a fragment thereof in the presence of a test compound to identify an agent that modulates the cellular activity of the IP3K. In some methods, the IP3K employed is an IP3KB. In some methods, the test compound inhibits kinase activity of the IP3K. These methods can further comprise testing the identified agents for ability to modulate T cell differentiation. T cell differentiation to be tested can be development of CD4+ CD8+ T cells into CD4+ or CD8+ mature T cells.

In a related aspect, the invention provides for identifying agents that modulate T lymphocyte differentiation. These methods comprise (a) assaying a cellular activity of an inositol 1,4,5-trisphosphate 3-kinase (also termed IP3K or ITPK) or a fragment thereof in the presence of a test agent to identify one or more modulating agents that modulate the cellular activity of the IP3KB (also termed ITPKB), and (b) testing one or more of the modulating agents for ability to modulate T lymphocyte development or function.

In some of these methods, the test compound inhibits kinase activity of the IP3K. Some methods assay the kinase activity in catalyzing conversion of inositol 1,4,5-triphosphate (IP3) to inositol 1,3,4,5-tetrakisphosphate (IP4). In some methods, the IP3K employed is an IP3KB. The IP3KB employed can have the amino acid sequence of Accession No. CAB65055, Accession No. CAC40660, Accession No. NP_002212 or that of SEQ ID NO: 1, or that is substantially identical to any of these sequences. It can also be encoded by a polynucleotide having a nucleotide sequence that is shown in SEQ ID NO: 2, 3, or 4, or that is substantial identical to any of these sequences.

In some other methods, the modulating agents decrease cellular levels of the IP3K. The cells can be selected from the group consisting of thymus cells, CD4+ CD8+ T cells, CD4+ T cells, CD8+ T cells, and NK cells. In some of these methods, the modulating agents inhibit expression of a gene encoding the IP3K.

In another aspect, the invention provides methods for suppressing an undesired T lymphocyte response in a subject. Such methods comprise administering to the subject an effective amount of an agent that inhibits a cellular activity of an IP3K, thereby suppressing T lymphocyte responses in the subject. Some of these methods are directed to subjects that suffer from an autoimmune disease or graft rejection. Examples of autoimmune diseases that are amenable to these methods include systemic lupus erythematosus (SLE), rheumatoid arthritis (RA), or multiple sclerosis (MS).

In another related aspect, the invention provides methods for modulating T lymphocyte differentiation in a subject. The methods comprise (a) screening test compounds to identify a modulating agent that modulates a cellular activity of an IP3K, and (b) administering to the subject a pharmaceutical composition comprising an effective amount of the modulating agent; thereby modulating T lymphocyte differentiation in the subject.

In another aspect, the invention provides methods for treating a disease or disorder in a subject, e.g., inflammation, graft versus host disease, psoriasis, or allergy (asthma, rhinitis, COPD, and dermatitis). These methods entail screening test compounds to identify a modulating agent that modulates a cellular activity of an IP3K, and then administering to the subject a pharmaceutical composition comprising an effective amount of the modulating agent; thereby treating the disease or disorder in the subject.

A further understanding of the nature and advantages of the present invention may be realized by reference to the remaining portions of the specification and claims.

DESCRIPTION OF THE PREFERRED EMBODIMENTS

I. Overview

Figure 1:
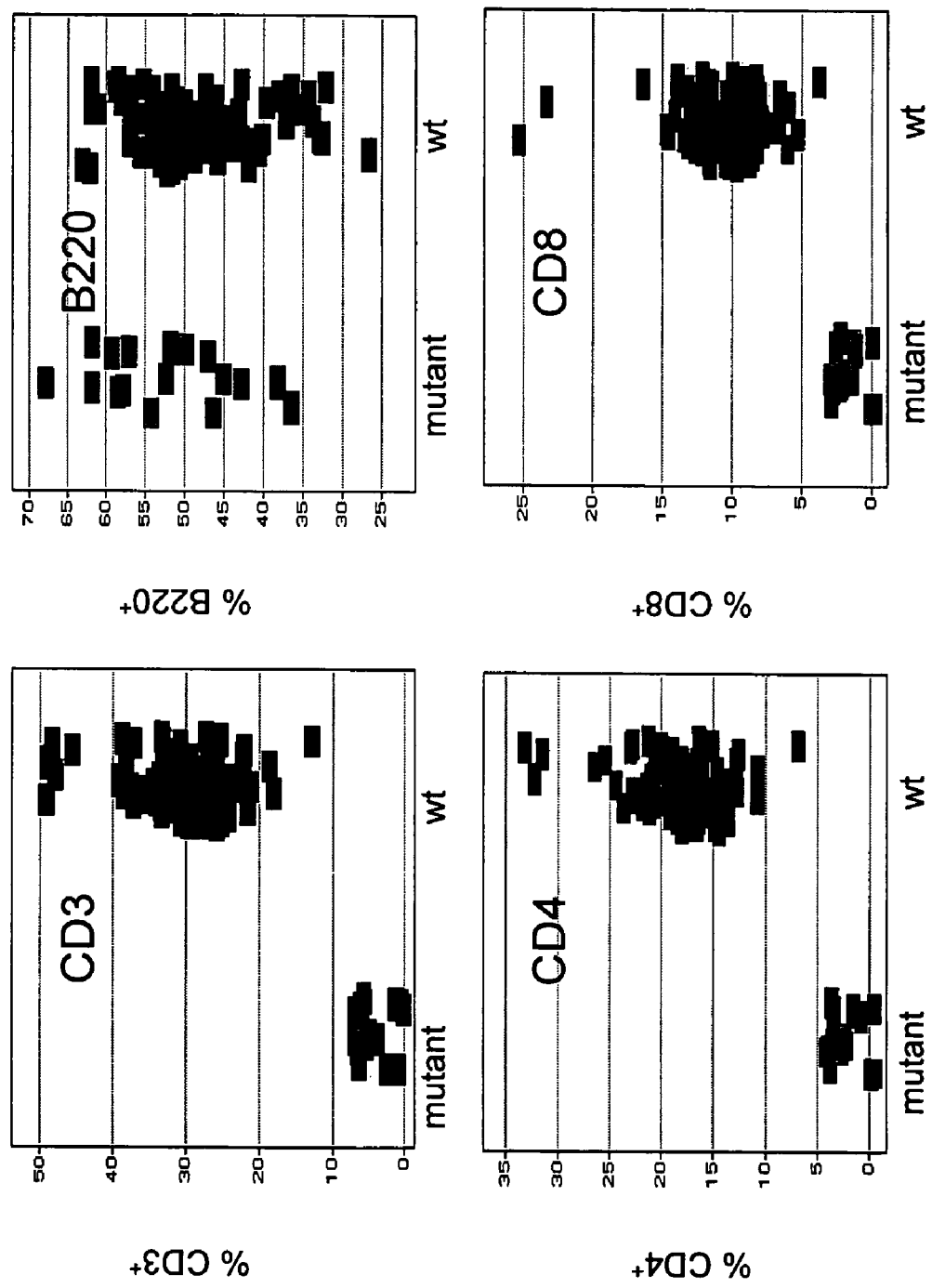
FIG. 1 shows that numbers of peripheral blood CD4+ and CD8+ T cells, but not B cells, are drastically reduced in Ms. T-less mutant mice.

The invention is predicated in part on the discovery by the present inventors that a gene not known to be involved in T or B cell development plays an important and essential role in T cell development and function. It was found that a mouse with a recessive mutant in the inositol 1,4,5-trisphosphate 3-kinase B (IP3KB or ITPKB) gene lacks any T cells in the peripheral blood and displays a moderate perturbation of transitional B cell development in the spleen (termed "Ms. T-less mice"). The IP3KB gene was mapped to a small portion of chromosome 1. There are no genes in this region which are known to be involved in T or B cell development.

As detailed in the Examples below, closer analysis of T cell development in the thymus revealed a complete block at the CD4+ CD8+ double positive (DP) stage with no CD4+ or CD8+ single positive (SP) cells present. Expression analysis of activation markers and T cell receptor (TCR) associated genes suggests that the DP cells in Ms. T-less mice are not receiving or improperly translating differentiation signals originating from the TCR. However, there were no significant effects on calcium responses in TCR-stimulated CD4+ CD8+ T cells from mice with this mutant IP3KB gene. Instead, it was found that there is a specific defect in the activation of Erk, a critical mediator of positive selection. This indicates that the present inventors have identified a novel and important component of lymphocyte maturation, i.e., revealing IP3KB as a unique and novel link between the TCR and the Ras-MAP kinase pathway which is essential for T cell development.

In accordance with these discoveries, the present invention provides methods for screening novel agents that modulate T cell development and function. Test agents are examined for their ability to modulate a cellular activity (e.g., cellular level or kinase activity) of an inositol 1,4,5-trisphosphate 3-kinase. Various IP3K enzymes can be employed in the screening assays. For example, either IP3KA, IP3KB, or IP3KC from human, rat or mouse can be used to screen the modulators. In preferred embodiments, an IP3KB is used. In some preferred embodiments, the modulators identified in the screening assays inhibit IP3KB kinase activity or reduce its cellular level.

The invention also provides methods for modulating T cell development and function in a subject (including human and animals such as other mammals). The methods entail administering to a subject an IP3K modulator. The IP3K modulator can be identified in accordance with the present invention. Alternatively, the IP3K modulators employed in the methods can be IP3K inhibitors known in the art. For example, purine-based IP3K inhibitors are described in Chang et al., Chembiochem 3:897-901, 2002. In some preferred methods, IP3KB inhibitors are used to inhibit T cell development and function. By modulating T cell development or function, these IP3K modulators also find applications in treating various medical conditions where undesired immune responses mediated by T cells play a role. Accordingly, the invention also provides methods for treating conditions such as autoimmune diseases or other conditions with undesired T cell responses.

Transgenic or knockout animals (e.g., mice) that do not express endogenous IP3KB are also provided in the invention. The animals can either have a null allele in the IP3KB locus or a mutation in the IP3KB gene which results in no functional IP3KB protein being produced. For example, the Ms. T-less mice described in the Examples below have a premature STOP codon at amino acid position 199 within exon 2 of the IP3KB gene. This results in expression of a nonfunctional protein that lacks most of the IP3KB sequence. By blocking differentiation of progenitor T cells into mature CD4+ or CD8+ T cells, such animals provide useful tools to study T cell development and T cell immune responses.

The following sections provide guidance for making and using the compositions of the invention, and for carrying out the methods of the invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); and Hale & Marham, THE HARPER COLLINS DICTIONARY OF BIOLOGY (1991). In addition, the following definitions are provided to assist the reader in the practice of the invention.

The term "agent" or "test agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" can be used interchangeably.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved traits (such as higher binding affinity for a target molecule) is an approach that is well known in pharmaceutical chemistry.

As used herein, "contacting" has its normal meaning and refers to combining two or more agents (e.g., polypeptides or small molecule compounds) or combining agents and cells (e.g., a polypeptide and a cell). Contacting can occur in vitro, e.g., combining two or more agents or combining a test agent and a cell or a cell lysate in a test tube or other container. Contacting can also occur in a cell or in situ, e.g., contacting two polypeptides in a cell by coexpression in the cell of recombinant polynucleotides encoding the two polypeptides, or in a cell lysate.

A "heterologous sequence" or a "heterologous nucleic acid," as used herein, is one that originates from a source foreign to the particular host cell, or, if from the same source, is modified from its original form. Thus, a heterologous gene in a host cell includes a gene that, although being endogenous to the particular host cell, has been modified. Modification of the heterologous sequence can occur, e.g., by treating the DNA with a restriction enzyme to generate a DNA fragment that is capable of being operably linked to the promoter. Techniques such as site-directed mutagenesis are also useful for modifying a heterologous nucleic acid.

The term "homologous" when referring to proteins and/or protein sequences indicates that they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95% or 99% or more can also be used to establish homology. Methods for determining sequence similarity percentages (e.g., BLASTP and BLASTN using default parameters) are described herein or well known and readily available in the art.

A "host cell," as used herein, refers to a prokaryotic or eukaryotic cell that contains heterologous DNA that has been introduced into the cell by any means, e.g., electroporation, calcium phosphate precipitation, microinjection, transformation, viral infection, and/or the like.

The terms "identical" or "sequence identity" in the context of two nucleic acid sequences or amino acid sequences refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are aligned optimally. Methods of alignment of sequences for comparison are well known in the art. Optimal alignment of sequences for comparison may be conducted by the local homology algorithm of Smith and Waterman (1981) Adv. Appl. Math. 2:482; by the alignment algorithm of Needleman and Wunsch (1970) J. Mol. Biol. 48:443; by the search for similarity method of Pearson and Lipman (1988) Proc. Nat. Acad. Sci U.S.A. 85:2444; by computerized implementations of these algorithms (including, but not limited to CLUSTAL in the PC/Gene program by Intelligentics, Mountain View, Calif.; and GAP, BESTFIT, BLAST, FASTA, or TFASTA in the Wisconsin Genetics Software Package, Genetics Computer Group (GCG), 575 Science Dr., Madison, Wis., U.S.A.). The CLUSTAL program is well described by Higgins and Sharp (1988) Gene 73:237-244; Higgins and Sharp (1989) CABIOS 5:151-153; Corpet et al. (1988) Nucleic Acids Res. 16:10881-10890; Huang et al (1992) Computer Applications in the Biosciences 8:155-165; and Pearson et al. (1994) Methods in Molecular Biology 24:307-331. Alignment is also often performed by inspection and manual alignment. In one class of embodiments, the polypeptides herein are at least 70%, generally at least 75%, optionally at least 80%, 85%, 90%, 95% or 99% or more identical to a reference polypeptide, as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 95%, 99% or more identical to a reference nucleic acid, as measured by BLASTN (or CLUSTAL, or any other available alignment software) using default parameters.

The terms "substantially identical" nucleic acid or amino acid sequences means that a nucleic acid or amino acid sequence comprises a sequence that has at least 90% sequence identity or more, preferably at least 95%, more preferably at least 98% and most preferably at least 99%, compared to a reference sequence using the programs described above (preferably BLAST) using standard parameters. For example, the BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)). Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

The term "isolated" means that the material is removed from its original environment (e.g., the natural environment if it is naturally occurring). For example, a naturally-occurring nucleic acid, polypeptide, or cell present in a living animal is not isolated, but the same polynucleotide, polypeptide, or cell separated from some or all of the coexisting materials in the natural system, is isolated, even if subsequently reintroduced into the natural system. Such nucleic acids can be part of a vector and/or such nucleic acids or polypeptides could be part of a composition, and still be isolated in that such vector or composition is not part of its natural environment.

The terms "nucleic acid," "DNA sequence" or "polynucleotide" refer to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. A "polynucleotide sequence" is a nucleic acid (which is a polymer of nucleotides (A, C, T, U, G, etc. or naturally occurring or artificial nucleotide analogues) or a character string representing a nucleic acid, depending on context. Either the given nucleic acid or the complementary nucleic acid can be determined from any specified polynucleotide sequence.

The term "modulate" with respect to cellular activities of an IP3K refers to a change in the cellular level or other biological activities (e.g., kinase activity) of the IP3K enzyme. Modulation of IP3K activities can be up-regulation (i.e., activation or stimulation) or down-regulation (i.e. inhibition or suppression). For example, modulation may cause a change in cellular level of IP3K, enzymatic modification (e.g., phosphorylation) of IP3K, binding characteristics (e.g., binding to a substrate or ATP), or any other biological, functional, or immunological properties of IP3K proteins. The change in activity can arise from, for example, an increase or decrease in expression of the IP3K gene, the stability of mRNA that encodes the IP3K protein, translation efficiency, or from a change in other bioactivities of the IP3K enzymes (e.g., its kinase activity). The mode of action of an IP3K modulator can be direct, e.g., through binding to the IP3K protein or to a gene encoding the IP3K protein. The change can also be indirect, e.g., through binding to and/or modifying (e.g., enzymatically) another molecule which otherwise modulates IP3K.

The term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The term "operably linked" refers to a functional relationship between two or more polynucleotide (e.g., DNA) segments. Typically, it refers to the functional relationship of a transcriptional regulatory sequence to a transcribed sequence. For example, an IP3K promoter or enhancer sequence, is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance. A polylinker provides a convenient location for inserting coding sequences so the genes are operably linked to the IP3K promoter. Polylinkers are polynucleotide sequences that comprise a series of three or more closely spaced restriction endonuclease recognition sequences.

The term "polypeptide" is used interchangeably herein with the terms "polypeptides" and "protein(s)", and refers to a polymer of amino acid residues, e.g., as typically found in proteins in nature. A "mature protein" is a protein which is full-length and which, optionally, includes glycosylation or other modifications typical for the protein in a given cell membrane.

The promoter region of a gene includes the transcription regulatory elements that typically lie 5' to a structural gene. If a gene is to be activated, proteins known as transcription factors attach to the promoter region of the gene. This assembly resembles an "on switch" by enabling an enzyme to transcribe a second genetic segment from DNA into RNA. In most cases the resulting RNA molecule serves as a template for synthesis of a specific protein; sometimes RNA itself is the final product. The promoter region may be a normal cellular promoter or an oncopromoter.

Transcription refers to the process involving the interaction of an RNA polymerase with a gene, which directs the expression as RNA of the structural information present in the coding sequences of the gene. The process includes, but is not limited to the following steps: (1) transcription initiation, (2) transcript elongation, (3) transcript splicing, (4) transcript capping, (5) transcript termination, (6) transcript polyadenylation, (7) nuclear export of the transcript, (8) transcript editing, and (9) stabilizing the transcript.

A transcription regulatory element or sequence include, but is not limited to, a promoter sequence (e.g., the TATA box), an enhancer element, a signal sequence, or an array of transcription factor binding sites. It controls or regulates transcription of a gene operably linked to it.

A "variant" of a molecule such as an IP3K is meant to refer to a molecule substantially similar in structure and biological activity to either the entire molecule, or to a fragment thereof. Thus, provided that two molecules possess a similar activity, they are considered variants as that term is used herein even if the composition or secondary, tertiary, or quaternary structure of one of the molecules is not identical to that found in the other, or if the sequence of amino acid residues is not identical.

III. Inositol 1,4,5-trisphosphate 3-kinases (IP3Ks) Used in Screening

Inositol 1,4,5-trisphosphate 3-kinases (IP3Ks) are enzymes which catalyze the conversion of inositol 1,4,5-trisphosphate (Ins(1,4,5)$P_3$, or $IP_3$) to inositol 1,3,4,5-tetrakisphosphate (Ins(1,3,4,5)$P_4$ or IP4). IP3 and IP4 are potential modulators of calcium homoeostasis. There are three different isoforms of IP3K, IP3KA, IP3KB, and IP3KC. In the present invention, novel modulators of IP3K are identified by screening test agents for ability to modulate a cellular activity of an IP3K. The cellular activities to be monitored in the screening assays can be an enzymatic activity of the IP3K or its cellular level. Modulation of the cellular activity can be an up-regulation (to increase or stimulate) or a down-regulation (to decrease or inhibit). In preferred embodiments, test agents are screened for ability to inhibit the IP3K activity in catalyzing the conversion of IP3 to IP4.

Various IP3Ks can be employed in screening the IP3K modulators of the present invention. Preferably, an IP3KB molecule is used. In some methods, an IP3KB polypeptide having an amino acid sequence of Accession No. CAB65055, Accession No. CAC40660, Accession No. NP_002212 or SEQ ID NO: 1, or a substantial identical sequence, is employed in the screening assay. In some methods, an IP3K polypeptide that is encoded by a polynucleotide having the sequence of SEQ ID NO: 2, 3, or 4, or a substantial identical sequence, is used. SEQ ID NOS: 2, 3, and 4 respectively encode IP3KB from human, rat, and mouse.

Other than IP3K sequences disclosed herein, various IP3K sequences that have been described in the art can also be employed in the screening assays of the present invention. For example, different isoforms of IP3K have been identified in a number of species, see, e.g., Takazawa et al., Rat brain inositol 1,4,5-trisphosphate 3-kinase. Ca 2+-sensitivity, purification and antibody production. Biochem. J. 268, 213-217, 1990; Thomas et al., Isolation and sequence of a full length cDNA encoding a novel rat inositol 1,4,5-trisphosphate 3-kinase. Biochim. Biophys. Acta 1220, 219-222, 1994; Takazawa et al., Molecular cloning and expression of a human brain inositol 1,4,5-trisphosphate 3-kinase. Biochem. Biophys. Res. Commun. 174, 529-535, 1991; Takazawa et al., Molecular cloning and expression of a new putative inositol 1,4,5-trisphosphate 3-kinase isoenzyme. Biochem. J. 278, 883-886, 1991; Vanweyenberg et al., Tissue- and cell-specific expression of Ins(1,4,5)P 3 3-kinase isoenzymes. Biochem. J. 306, 429-435, 1995. Dewaste et al., Cloning and expression of a cDNA encoding human inositol 1,4,5-trisphosphate 3-kinase C. Biochem. J. 352: 343-351, 2000; Choi et al., Molecular cloning and expression of a complementary DNA for inositol 1,4,5-trisphosphate 3-kinase. Science 248: 64-66, 1990; and Mailleux et al., Astrocytic localization of the messenger RNA encoding the isoenzyme B of inositol (1,4,5) 3-kinase in the human brain. Neurosci. Lett. 148: 177-180, 1992. Yeast and *C. elegans* IP3Ks have also been described in the art. See, e.g., GenBank Accession Numbers P91166 and NP-010458 and Dewaste et al., Biochem. J. 352: 343-351, 2000. Additional IP3K sequences or fragments from various species have also been described in the art, e.g., amino acid sequences with Accession Numbers P27987, P23677, P17105, Q91XW1, CG1630, O45049, Q9Y475, Q9YH86, and Q963D4 (EC 2.7.1.127). Other polynucleotide sequences encoding human, mouse, or rat IP3Ks include, but are not limited to, accession numbers Y18024, NM002221, BC015009, AJ242780, AJ242781, AK0533759, AK050506, and NM019312. Any of these IP3K sequences can be used to screen test agents for modulators in the present invention.

In addition to an intact IP3K molecule or a polynucleotide encoding the intact IP3K molecule, an IP3K fragment, analog, or a functional derivative can also be used. The IP3K fragments that can be employed in these assays usually retain one or more of the biological activities of the IP3K molecule (typically, its kinase activity). For example, the three isoforms of IP3Ks share a conserved catalytic domain of about 275 amino acids (Dewaste et al., Biochem. J. 352: 343-351, 2000). ATP binding site and IP3 binding site are often also preserved in such fragments or analogs. Fusion proteins containing such fragments or analogs can also be used for the screening of test agents. Similarly, functional derivatives of IP3Ks usually have amino acid deletions and/or insertions and/or substitutions while maintaining one or more of the bioactivities. As noted above, IP3Ks from the different species have already been sequenced and well characterized. Therefore, their fragments, analogs, derivatives, or fusion proteins can be easily obtained using methods well known in the art. For example, a functional derivative of an IP3K can be prepared from a naturally occurring or recombinantly expressed protein by proteolytic cleavage followed by conventional purification procedures known to those skilled in the art. Alternatively, the functional derivative can be produced by recombinant DNA technology by expressing only fragments of an IP3K that retains its kinase activity.

IV. Test Agents

Test agents that can be screened with methods of the present invention include polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, structural analogs or combinations thereof. Some test agents are synthetic molecules, and others natural molecules.

Test agents are obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

Combinatorial libraries of peptides or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

The test agents can be naturally occurring proteins or their fragments. Such test agents can be obtained from a natural source, e.g., a cell or tissue lysate. Libraries of polypeptide agents can also be prepared, e.g., from a cDNA library commercially available or generated with routine methods. The test agents can also be peptides, e.g., peptides of from about 5 to about 30 amino acids, with from about 5 to about 20 amino acids being preferred, and from about 7 to about 15 being particularly preferred. The peptides can be digests of naturally occurring proteins, random peptides, or "biased" random peptides. In some methods, the test agents are polypeptides or proteins.

The test agents can also be nucleic acids. Nucleic acid test agents can be naturally occurring nucleic acids, random nucleic acids, or "biased" random nucleic acids. For example, digests of prokaryotic or eukaryotic genomes can be similarly used as described above for proteins.

In some preferred methods, the test agents are small molecules (e.g., molecules with a molecular weight of not more than about 1,000). Preferably, high throughput assays are adapted and used to screen for such small molecules. In some methods, combinatorial libraries of small molecule test agents as described above can be readily employed to screen for small molecule modulators of IP3Ks. A number of assays are available for such screening, e.g., as described in Schultz (1998) Bioorg Med Chem Lett 8:2409-2414; Weller (1997) Mol Divers. 3:61-70; Fernandes (1998) Curr Opin Chem Biol 2:597-603; and Sittampalam (1997) Curr Opin Chem Biol 1:384-91.

Libraries of test agents to be screened with the claimed methods can also be generated based on structural studies of the IP3K polypeptides, their fragments or analogs. Such structural studies allow the identification of test agents that are more likely to bind to the IP3K polypeptides. The three-dimensional structure of an IP3K polypeptide can be studied in a number of ways, e.g., crystal structure and molecular modeling. Methods of studying protein structures using x-ray crystallography are well known in the literature. See Physical Bio-chemistry, Van Holde, K. E. (Prentice-Hall, New Jersey 1971), pp. 221-239, and Physical Chemistry with Applications to the Life Sciences, D. Eisenberg & D. C. Crothers (Benjamin Cummings, Menlo Park 1979). Computer modeling of IP3K polypeptides' structures provides another means for designing test agents for screening IP3K modulators. Methods of molecular modeling have been described in the literature, e.g., U.S. Pat. No. 5,612,894 entitled "System and method for molecular modeling utilizing a sensitivity factor", and U.S. Pat. No. 5,583,973 entitled "Molecular modeling method and system". In addition, protein structures can also be determined by neutron diffraction and nuclear magnetic resonance (NMR). See, e.g., Physical Chemistry, 4th Ed. Moore, W. J. (Prentice-Hall, New Jersey 1972), and NMR of Proteins and Nucleic Acids, K. Wuthrich (Wiley-Interscience, New York 1986).

Modulators of the present invention also include antibodies that specifically bind to an IP3K polypeptide. Such antibodies can be monoclonal or polyclonal. Such antibodies can be generated using methods well known in the art. For example, the production of non-human monoclonal antibodies, e.g., murine or rat, can be accomplished by, for example, immunizing the animal with an IP3K polypeptide or its fragment (See Harlow & Lane, Antibodies, A Laboratory Manual, Cold Spring Harbor Laboratory Press, Cold Spring Harbor N.Y.).

Such an immunogen can be obtained from a natural source, by peptides synthesis or by recombinant expression.

Humanized forms of mouse antibodies can be generated by linking the CDR regions of non-human antibodies to human constant regions by recombinant DNA techniques. See Queen et al., Proc. Natl. Acad. Sci. USA 86, 10029-10033 (1989) and WO 90/07861. Human antibodies can be obtained using phage-display methods. See, e.g., Dower et al., WO 91/17271; McCafferty et al., WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to an IP3K polypeptide of the present invention.

Human antibodies against an IP3K polypeptide can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991). Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using an IP3K polypeptide or its fragment.

V. Screen Test Agents for IP3K Modulators

Employing an IP3K polypeptide described above, the present invention provides methods for screening agents or compounds that modulate cellular activities (e.g., kinase activity or cellular level) of IP3Ks. In some preferred embodiments, test agents are screened for ability to modulate (e.g., inhibit) IP3K activity in catalyzing IP3 conversion to IP4. A variety of routinely practiced assays can be used to identify test agents that modulate kinase activity of an IP3K. For example, inhibitors of an IP3K can be identified in a soluble assay format as described in Chang et al., Chembiochem 3:897-901, 2002. Dewaste et al. (Biochem. J. 352: 343-351, 2000) disclosed a method wherein IP3K kinase activity was determined in bacteria and in transfected cells under basal conditions. Woodring et al. (J. Biol. Chem. 272: 30447-54, 1997) also described IP3K activity assays. These assays often use labeled or unlabeled IP3 and ATP in the presence of an IP3K kinase and a test agent. High performance liquid chromatography (HPLC) can be used to quantitated IP4 in the reaction product. Alternatively, conversion of IP3 to IP4 can be determined by measuring radioactivity incorporated into IP4 when IP3 used in the reaction is radiolabeled (Chang et al., Chembiochem 3: 897-901, 2002). IP3K activity can also be monitored by the kinase glow assay. This assay measures the disappearance of labeled ATP once it has been used to phosphorylate the substrate. With this assay format, the requirement for detecting the formation of IP4 from IP3 can be bypassed. The kinase glow assay is well known and routinely practiced in the art, e.g., as described in Somberg et al., Promega Notes, 83: 14-17, 2003. Any of these assays can be readily adopted in the present invention to screen for modulators of IP3K kinase activity.

In some methods, test agents can be first screened for their ability to bind to an IP3K polypeptide. Compounds thus identified can be further subject to assay for ability to modulate (e.g., to inhibit) IP3K kinase activity as described above. Binding of test agents to an IP3K polypeptide can be assayed by a number of methods including, e.g., labeled in vitro protein-protein binding assays, electrophoretic mobility shift assays, immunoassays for protein binding, functional assays (phosphorylation assays, etc.), and the like. See, e.g., U.S. Pat. Nos. 4,366,241; 4,376,110; 4,517,288; and 4,837,168; and also Bevan et al., Trends in Biotechnology 13:115-122, 1995; Ecker et al., Bio/Technology 13:351-360, 1995; and Hodgson, Bio/Technology 10:973-980, 1992. The test agent can be identified by detecting a direct binding to the IP3K polypeptide, e.g., co-immunoprecipitation with the IP3K polypeptide by an antibody directed to the IP3K polypeptide. The test agent can also be identified by detecting a signal that indicates that the agent binds to the IP3K polypeptide, e.g., fluorescence quenching.

Competition assays provide a suitable format for identifying test agents that specifically bind to an IP3K polypeptide. In such formats, test agents are screened in competition with a compound already known to bind to the IP3K polypeptide. The known binding compound can be a synthetic compound. It can also be an antibody, which specifically recognizes the IP3K polypeptide, e.g., a monoclonal antibody directed against the IP3K polypeptide. If the test agent inhibits binding of the compound known to bind the IP3K polypeptide, then the test agent also binds the IP3K polypeptide.

Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242-253 (1983)); solid phase direct biotin-avidin EIA (see Kirkland et al., J. Immunol. 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using $^{125}$I label (see Morel et al., Mol. Immunol. 25(1):7-15 (1988)); solid phase direct biotin-avidin EIA (Cheung et al., Virology 176:546-552 (1990)); and direct labeled RIA (Moldenhauer et al., Scand. J. Immunol. 32:77-82 (1990)). Typically, such an assay involves the use of purified polypeptide bound to a solid surface or cells bearing either of these, an unlabelled test agent and a labeled reference compound. Competitive inhibition is measured by determining the amount of label bound to the solid surface or cells in the presence of the test agent. Usually the test agent is present in excess. Modulating agents identified by competition assay include agents binding to the same epitope as the reference compound and agents binding to an adjacent epitope sufficiently proximal to the epitope bound by the reference compound for steric hindrance to occur. Usually, when a competing agent is present in excess, it will inhibit specific binding of a reference compound to a common target polypeptide by at least 50 or 75%.

The screening assays can be either in insoluble or soluble formats. One example of the insoluble assays is to immobilize an IP3K polypeptide or its fragments onto a solid phase matrix. The solid phase matrix is then put in contact with test agents, for an interval sufficient to allow the test agents to bind. Following washing away any unbound material from the solid phase matrix, the presence of the agent bound to the solid phase allows identification of the agent. The methods can further include the step of eluting the bound agent from the solid phase matrix, thereby isolating the agent. Alternatively, other than immobilizing the IP3K polypeptide, the test agents are bound to the solid matrix and the IP3K polypeptide molecule is then added.

Soluble assays include some of the combinatory libraries screening methods. Under the soluble assay formats, neither the test agents nor the IP3K polypeptide are bound to a solid support. Binding of an IP3K polypeptide or fragment thereof to a test agent can be determined by, e.g., changes in fluorescence of either the IP3K polypeptide or the test agents, or both. Fluorescence may be intrinsic or conferred by labeling either component with a fluorophor.

In some binding assays, either the IP3K polypeptide, the test agent, or a third molecule (e.g., an antibody against the IP3K polypeptide) can be provided as labeled entities, i.e., covalently attached or linked to a detectable label or group, or cross-linkable group, to facilitate identification, detection and quantification of the polypeptide in a given situation. These detectable groups can comprise a detectable polypeptide group, e.g., an assayable enzyme or antibody epitope. Alternatively, the detectable group can be selected from a variety of other detectable groups or labels, such as radiolabels (e.g., $^{125}$I, $^{32}$P, $^{35}$S) or a chemiluminescent or fluorescent group. Similarly, the detectable group can be a substrate, cofactor, inhibitor or affinity ligand.

In some other methods, test agents are assayed for activity to modulate cellular levels of the IP3K polypeptide, e.g., transcription or translation. The test agent can also be assayed for activities in modulating expression level or stability of the IP3K polypeptide, e.g., post-translational modification or proteolysis. Various biochemical and molecular biology techniques well known in the art can be employed to practice the present invention. Such techniques are described in, e.g., Sambrook et al., *Molecular Cloning: A Laboratory Manual*, Cold Spring Harbor Press, N.Y., Second (1989) and Third (2000) Editions; and Ausubel et al., *Current Protocols in Molecular Biology*, John Wiley & Sons, Inc., New York (1987-1999). In some embodiments, endogenous levels of an IP3KB can be directly monitored in cells normally expressing this enzyme (e.g., thymus cells). In some embodiments, expression or cellular level of an IP3K can be can be examined in an expression system using cloned cDNA or genomic sequence encoding the IP3K.

Alternatively, modulation of expression of an IP3K gene can be examined in a cell-based system by transient or stable transfection of an expression vector into cultured cell lines. Assay vectors bearing transcription regulatory sequence (e.g., promoter) of an IP3K gene operably linked to reporter genes can be transfected into any mammalian host cell line for assays of promoter activity. Constructs containing an IP3K gene (or a transcription regulatory element of an IP3K gene) operably linked to a reporter gene can be prepared using only routinely practiced techniques and methods of molecular biology (see, e.g., Sambrook et al. and Ausubel et al., supra). General methods of cell culture, transfection, and reporter gene assay have been described in the art, e.g., Ausubel, supra; and Transfection Guide, Promega Corporation, Madison, Wis. (1998). Any readily transfectable mammalian cell line may be used to assay IP3K promoter function, e.g., HCT116, HEK 293, MCF-7, and HepG2 are all suitable cell lines.

When inserted into the appropriate host cell, the transcription regulatory elements in the expression vector induces transcription of the reporter gene by host RNA polymerases. Reporter genes typically encode polypeptides with an easily assayed enzymatic activity that is naturally absent from the host cell. Typical reporter polypeptides for eukaryotic promoters include, e.g., chloramphenicol acetyltransferase (CAT), firefly or Renilla luciferase, beta-galactosidase, beta-glucuronidase, alkaline phosphatase, and green fluorescent protein (GFP).

VI. Modulation of T Cell Differentiation and Function

The present invention provides compositions and methods for modulating T cell development and functions. As a consequence of the connection between the IP3K and T cell development, modulation of cellular levels or kinase activity of IP3Ks (e.g., IP3KB) can lead to modulation of T cell function and immune response mediated by T cells. To identify such modulators of T cells, an IP3K modulator described above can be further examined to confirm its ability to modulate T cell differentiation.

As noted above, T lymphocyte differentiation proceeds through a series of discrete developmental stages. The progenitor cells (CD4$^-$CD8$^-$) first differentiate into double positive (DP) T cells (CD4$^+$ CD8$^+$ cells). The DP T cells then further develop into one of the mature, single positive (SP) T cells, CD4$^+$ CD8$^-$ or CD4$^-$ CD8$^+$. T cell progenitor cells as used herein therefore include pluripotent cells which are capable of self-renewal and differentiation into all myeloid and lymphoid cell lineages, including T cells.

Unless otherwise specified, "T cell differentiation" is used interchangeably herein with "T cell development" or "T cell maturation." These terms encompass the various stages of the process in which CD34+ progenitor cells develop into mature SP CD4+ or CD8+ T cells. Accordingly, activity of an IP3K modulator on T cell differentiation can be examined at any of these development stages. Modulation of T cell development can be examined using progenitor T cells at these various stages. In some embodiments, T cell development being modulated specifically refers to the development stage during which the DP (CD4+ CD8+) T cells develop into SP (CD4+ or CD8+) T cells.

T cell progenitor cells may be isolated from sources including bone marrow, umbilical cord blood or peripheral blood mobilized stem cells. Peripheral blood mobilized stem cells are obtained from the peripheral blood of subjects who have been treated with chemotherapeutic agents and/or cytokines to increase hematopoietic progenitor cells circulating in peripheral blood. The preferred hematopoietic T cell progenitor cells are those derived from humans. Progenitor cells at various stages of differentiation may be used in the present invention.

In some methods of the invention, modulation of T cell development by an IP3K modulating agent can be examined in vitro using thymic stromal cells derived from the disaggregation of a piece of thymus tissue. As described in, e.g., U.S. Pat. No. 5,677,139, this assay system is capable of supporting in vitro T cell growth and differentiation. Thymic stromal cells provide the supporting microenvironment in the intact thymus for the differentiation of T cell progenitor cells to mature T cells. The microenvironment includes soluble and cell surface factors expressed by the various cell types which comprise the thymic stroma.

Thymic stroma cells may be obtained from the thymus of a mammal (e.g., mice) or of a non-human primate at any time after the organ has developed to a stage at which it can support the differentiation of T cells. In primates, this stage of thymic development is achieved during the second trimester. At this stage of development the thymus can produce peptide hormones such as thymulin, thymosin, and thymopoietin, as well as other factors required to provide the proper microenvironment for T cell differentiation. It is preferred that the stromal cells are derived from a non-human primate thymus during the third trimester of gestation or from a thymus of a non-human primate neonate. During the mid to late third trimester, the thymus stromal microenvironment is fully capable of inducing the differentiation of T cell progenitor cells to mature T cells. The non-human primate stromal cells can be derived from any non-human primate. Examples include monkey, chimpanzee, and baboon.

In some other embodiments, other than using an in vitro system such as thymic stroma cells, modulating activity on T cell development is examined using an animal harboring an IP3K (e.g., IP3KB). The animal can endogenously express an IP3K (e.g., mice expressing mouse IP3KB). Alternatively, a transgenic mouse containing human IP3KB gene can be employed to study in vivo activity of a test agent or a pre-screened IP3K modulator on T cell development. Typically, thymi from transgenic mice administered with the IP3K modulating compound can be analyzed at various differentiation stages. For example, they can be analyzed by flow cytometry using antibodies against the different antigen markers of the T cells (e.g., antibodies against CD4 and CD8).

Transgenic animals (e.g., transgenic mice) harboring a heterologous IP3K gene (e.g., the human IP3KB gene) can be generated according to methods well known in the art. For example, techniques routinely used to create and screen for transgenic animals have been described in, e.g., see Bijvoet (1998) Hum. Mol. Genet. 7:53-62; Moreadith (1997) J. Mol. Med. 75:208-216; Tojo (1995) Cytotechnology 19:161-165; Mudgett (1995) Methods Mol. Biol. 48:167-184; Longo (1997) Transgenic Res. 6:321-328; U.S. Pat. Nos. 5,616,491 (Mak, et al.); 5,464,764; 5,631,153; 5,487,992; 5,627,059; 5,272,071; and WO 91/09955, WO 93/09222, WO 96/29411, WO 95/31560, and WO 91/12650.

In some embodiments, an IP3K gene linked to a reporter gene is injected into the embryo of a developing animal (typically a mouse) to generate a transgenic animal. Once integration of the transgene has been verified, tissues of the animal (e.g., lymphoid tissues) are then assayed for expression of the transgene. For example, where the IP3K gene is linked to a reporter gene, tissues of the transgenic animal may be assayed either for reporter gene RNA or for the enzymatic activity of the reporter polypeptide.

VII. Therapeutic Applications

The invention provides therapeutic compositions and methods for preventing or treating diseases and conditions due to abnormal T cell development or functions. For example, subjects with diseases or disorders such as inflammation, graft versus host disease, psoriasis, or allergy (asthma, rhinitis, COPD, and dermatitis) are all amenable to treatment with methods and compositions of the present invention. Specific and selective inhibition of an IP3K kinase (e.g., IP3KB) in T cells can inhibit T cell maturation, activation and function, resulting in profound immunosuppression. For example, IP3KB specifically accumulates only in the brain and in T cells or lymphoid tissues containing high numbers of T cells. Therefore, selective IP3KB inhibitors could prove highly tissue and even cell type specific. This will reduce the likelihood of adverse side reactions and general toxicity. As a result, therapeutic compositions comprising selective IP3KB-inhibitors of the present invention are advantageous over currently used immunosuppression drugs such as cyclosporine. The latter has severe side effects due to its pleiotrophic action.

Thus, the IP3K modulators of the present invention (e.g., a specific and selective IP3KB inhibitor) provide novel and less toxic immunosuppressants than those currently in clinical use. They are useful in the treatment of various medical conditions. In addition, other than the novel IP3K modulators of the present invention, IP3K inhibitors that are known in the art can also be employed in the therapeutic methods of the present invention (e.g., purine-based IP3K inhibitors as described in Chang et al., Chembiochem 3:897-901, 2002). Examples of the medical conditions include inflammatory responses in transplant rejection, autoimmune disease (e.g. systemic lupus erythematosus, rheumatoid arthritis, and multiple sclerosis), graft rejection and graft versus host disease, psoriasis, allergy (asthma, rhinitis, COPD, dermatitis), and others. In addition to treating these diseases or conditions, IP3K modulators of the present invention (e.g., IP3KB inhibitors) are also useful for preventing or modulating the development of such diseases or disorders in a subject (including human and animals such as other mammals) suspected of being, or known to be, prone to such diseases or disorders. In some applications, an IP3K inhibitor of the present invention can also be administered to a subject along with known immunosuppressive drugs such as cyclosporin.

The IP3K modulators of the present invention can be directly administered under sterile conditions to the subject to be treated. The modulators can be administered alone or as the active ingredient of a pharmaceutical composition. The therapeutic composition of the present invention can also be combined with or used in association with other therapeutic agents.

Pharmaceutical compositions of the present invention typically comprise at least one active ingredient together with one or more acceptable carriers thereof. Pharmaceutically carriers enhance or stabilize the composition, or to facilitate preparation of the composition. Pharmaceutically acceptable carriers are determined in part by the particular composition being administered (e.g., nucleic acid, protein, modulatory compounds or transduced cell), as well as by the particular method used to administer the composition. They should also be both pharmaceutically and physiologically acceptable in the sense of being compatible with the other ingredients and not injurious to the subject. This carrier may take a wide variety of forms depending on the form of preparation desired for administration, e.g., oral, sublingual, rectal, nasal, or parenteral. For example, the IP3K modulator can be complexed with carrier proteins such as ovalbumin or serum albumin prior to their administration in order to enhance stability or pharmacological properties.

There are a wide variety of suitable formulations of pharmaceutical compositions of the present invention (see, e.g., *Remington: The Science and Practice of Pharmacy*, Mack Publishing Co., 20$^{th}$ ed., 2000). Without limitation, they include syrup, water, isotonic saline solution, 5% dextrose in water or buffered sodium or ammonium acetate solution, oils, glycerin, alcohols, flavoring agents, preservatives, coloring agents starches, sugars, diluents, granulating agents, lubricants, and binders, among others. The carrier may also include a sustained release material such as glyceryl monostearate or glyceryl distearate, alone or with a wax.

The pharmaceutical compositions can be prepared in various forms, such as granules, tablets, pills, suppositories, capsules, suspensions, salves, lotions and the like. The concentration of therapeutically active compound in the formulation may vary from about 0.1-100% by weight. Therapeutic formulations are prepared by any methods well known in the art of pharmacy. See, e.g., Gilman et al., eds., Goodman and Gilman's: The Pharmacological Bases of Therapeutics, 8th ed., Pergamon Press, 1990; Remington: The Science and Practice of Pharmacy, Mack Publishing Co., 20$^{th}$ ed., 2000; Avis et al., eds., Pharmaceutical Dosage Forms: Parenteral Medications, published by Marcel Dekker, Inc., N.Y., 1993; Lieberman et al., eds., Pharmaceutical Dosage Forms: Tablets, published by Marcel Dekker, Inc., N.Y., 1990; and Lieberman et al., eds., Pharmaceutical Dosage Forms: Disperse Systems, published by Marcel Dekker, Inc., N.Y., 1990.

The therapeutic formulations can be delivered by any effective means which could be used for treatment. Depending on the specific IP3K modulators to be administered, the suitable means include oral, rectal, vaginal, nasal, pulmonary administration, or parenteral (including subcutaneous, intramuscular, intravenous and intradermal) infusion into the bloodstream. They can also be administered in eye drops or topical skin application.

For parenteral administration, IP3K modulators of the present invention may be formulated in a variety of ways. Aqueous solutions of the modulators may be encapsulated in polymeric beads, liposomes, nanoparticles or other injectable depot formulations known to those of skill in the art. The nucleic acids may also be encapsulated in a viral coat.

Additionally, the compounds of the present invention may also be administered encapsulated in liposomes. The compositions, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such a diacetylphosphate, stearylamine, or phosphatidic acid, and/or other materials of a hydrophobic nature.

The compositions may be supplemented by active pharmaceutical ingredients, where desired. Optional antibacterial, antiseptic, and antioxidant agents may also be present in the compositions where they will perform their ordinary functions.

The therapeutic formulations can conveniently be presented in unit dosage form and administered in a suitable therapeutic dose. A suitable therapeutic dose can be determined by any of the well known methods such as clinical studies on mammalian species to determine maximum tolerable dose and on normal human subjects to determine safe dosage. Except under certain circumstances when higher dosages may be required, the preferred dosage of an IP3K modulator usually lies within the range of from about 0.001 to about 1000 mg, more usually from about 0.01 to about 500 mg per day.

The preferred dosage and mode of administration of an IP3K modulator can vary for different subjects, depending upon factors that can be individually reviewed by the treating physician, such as the condition or conditions to be treated, the choice of composition to be administered, including the particular IP3K modulator, the age, weight, and response of the individual subject, the severity of the subject's symptoms, and the chosen route of administration. As a general rule, the quantity of an IP3K modulator administered is the smallest dosage which effectively and reliably prevents or minimizes the conditions of the subjects. Therefore, the above dosage ranges are intended to provide general guidance and support for the teachings herein, but are not intended to limit the scope of the invention.

In some applications, a first IP3K modulator is used in combination with a second IP3K modulator in order to modulate T cell development and function to a more extensive degree than cannot be achieved when one IP3K modulator is used individually.

EXAMPLES

The following examples are offered to illustrate, but not to limit the present invention.

Example 1

Generation of Ms. T-less Mice

This Example describes identification of mice that harbor N-ethyl-N-nitrosourea (ENU) induced homozygous recessive mutations in the IP3KB gene. Male C57/BL6 mice are injected with ENU (3 weekly injections of 85 mg ENU/kg mouse) and bred to a normal female C57/BL6 mouse to generate G1 offspring. Male G1s are then bred to normal female C57/BL6 mice to generate G2s. Female G2s are then backcrossed to G1 fathers to generate G3 mice which are phenotyped for homozygous recessive mutations. To identify immune mutants, mice at six to eight weeks of age are bled and lymphocyte populations are analyzed by flow cytometry.

Mice with a mutant phenotype thus identified are outcrossed to a different mouse strain which differs from C57BL/6 in multiple single nucleotide polymorphisms (SNPs) to generate F1s. For Ms. T-less and most immune mutants identified, we have chosen 129/SVImJ as the preferred mapping strain. F1s are intercrossed to generate F2s which are phenotyped and then subjected to SNP mapping to identify chromosomal regions that are homozygous C57B1/6J only in the affected animals. Concurrently, affected G3 animals are crossed to C57B1/6J to determine heritability of the mutation.

Example 2

Figure 2:
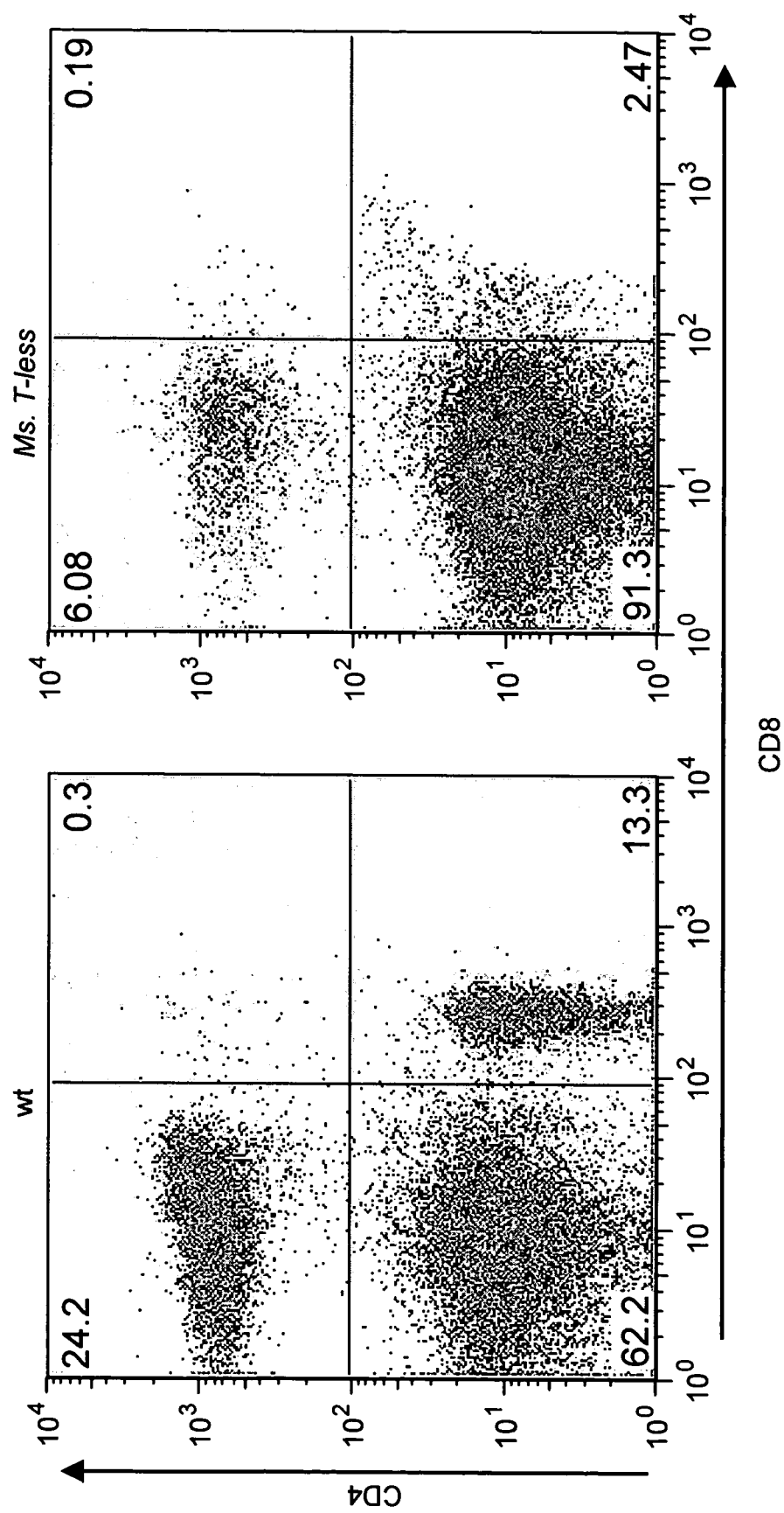
FIG. 2 shows that that spleens from Ms. T-less mutant mice are devoid of CD4+ and CD8+ T cells.

Characterization of T Cell Development in Ms. T-less Mutant Mice Lacking Functional IP3KB This Example describes effects of the Ms. T-less mutation on T cell development and functions. Ms. T-less (family 7) is a mutant that exhibits very few T cells in the peripheral blood, based on results from analyses of CD3 expression in peripheral blood lymphocyte populations. It was found that peripheral blood CD4+ and CD8+ T cells, but not B cells, are drastically reduced in Ms. T-less mutant mice. As shown in FIG. 1, peripheral blood lymphocytes from mutant (squares on the left side of each panel) and control (wt, squares on the right side of each panel) mice on a C57B1/6J background were stained with antibodies to CD3, B220, CD4, and CD8. The Scatter plots show lymphocyte subpopulations as percentages of total lymphocytes. Mutants exhibit a profound reduction in T cell, but not B cell, percentages when compared to wildtype mice. Further, splenocytes from mutant and wildtype mice were stained with antibodies against CD4 and CD8 and analyzed by flow cytometry. As shown in FIG. 2, spleens from Ms. T-less mutant mice are devoid of CD4+ and CD8+ T cells. Ms. T-less mice show drastically reduced T cell populations in the spleen. In older mice, however, there does seem to be a small accumulation of CD4+ cells. Numbers represent the percentage of cells within each quadrant.

In addition, T cells from mutant mice exhibit an activated phenotype. Splenocytes from mutant and wt mice were isolated and stained with antibodies against CD4, CD8, CD44, and TCRβ. The few CD4+ T cells seen in aged Ms. T-less mice do express TCRβ. The results also indicate elevated expression of CD44. Expression of the TCRβ chain and high levels of CD44 suggest that these cells may have expanded in a manner reminiscent of homeostatic proliferation to fill a lymphopenic environment.

Figure 3:
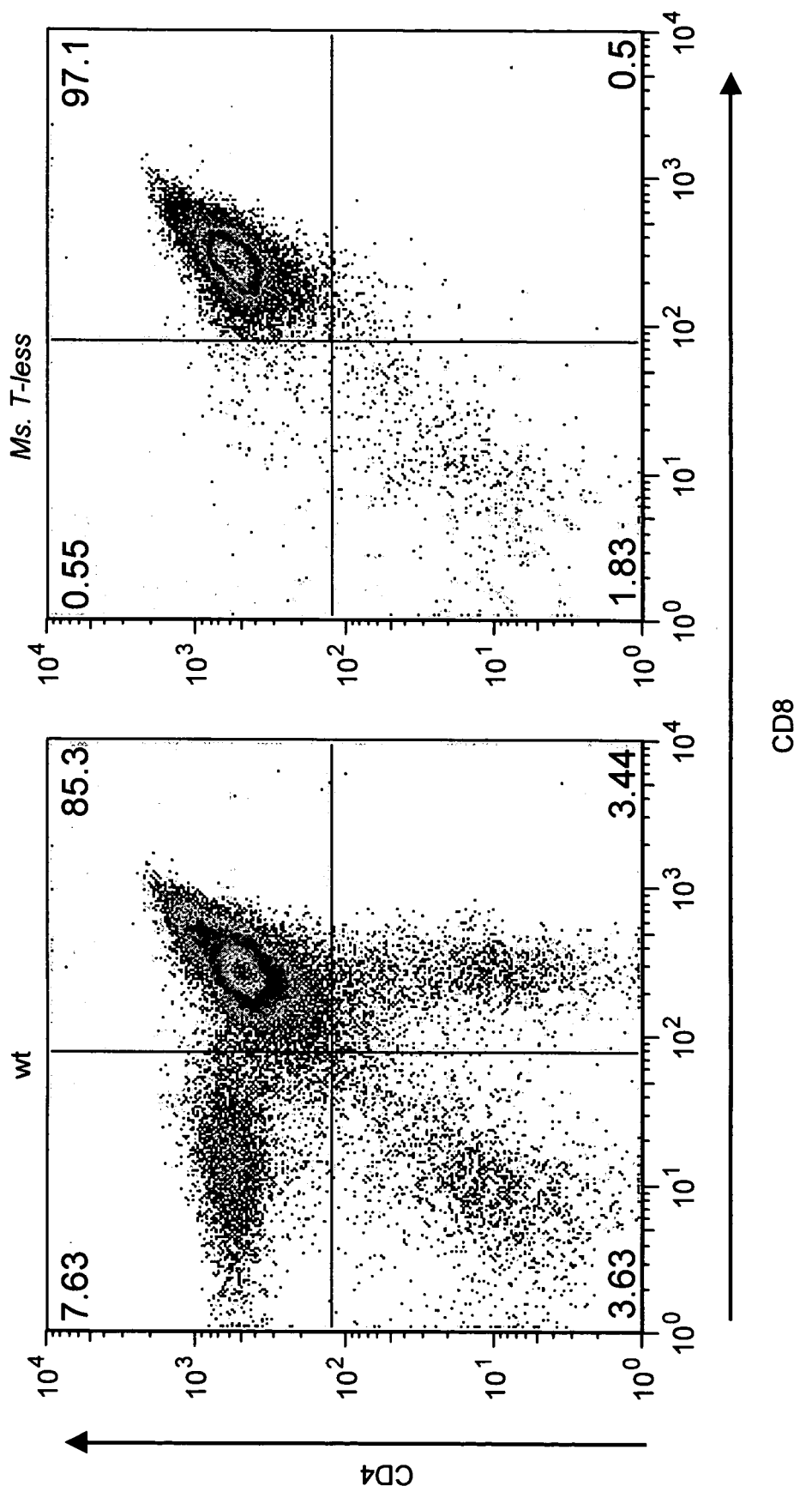
FIG. 3 shows that Ms. T-less mice exhibit a block of T cell development at the double positive (DP) stage.

As indicated in FIG. 3, the Ms. T-less mice exhibit a block in T cell development at the double positive (DP) stage. Thymi from mutant and wt mice were analyzed by flow cytometry using antibodies against CD4 and CD8. Ms. T-less mutant mice reveal an almost complete block at the CD4+ CD8+ double positive (DP) to CD4+ CD8− or CD4− CD8+ single positive (SP) transition. Numbers represent the percentage of cells in each quadrant.

Thymocytes from mutant and wt mice were analyzed by flow cytometry using antibodies against CD4, CD8, and TCRγδ. The results indicate that TCRγδ T cell development in the Ms. T-less mutant appears to be normal. TCRγδ T cells differentiate from TCRαβ T cells prior to the DP stage. Therefore, the developmental block in Ms. T-less mice is specific for the TCRαβ T cell compartment, likely resulting from a specific defect in thymic selection rather than a generalized impairment of T cell development.

It was found that DP thymocytes from Ms. T-less mice are not being selected. Expression analysis of activation markers and T cell receptor (TCR) associated genes suggests that the DP cells in the Ms. T-less mice are not receiving or improperly translating differentiation signals originating from the TCR. Thymi from mutant and wt mice were analyzed by flow cytometry using antibodies against CD4, CD8, CD69, and CD3 to follow T cell development. Shown in the figure are expression of CD69 and CD3 on CD4+ CD8+ DP cells. The results indicate that DP cells from Ms. T-less mice are not being properly selected as evidenced by lack of expression of activation markers such as CD69 and a lack of CD3$^{hi}$ cells.

In addition, the thymic cellularity of mutant and wt mice was determined by Trypan blue exclusion. Cell numbers were normalized to those observed in sex and age-matched wt littermate controls. Cellularity is expressed as a fold change value of the mutants over wt (for this analysis, n=8). The results indicate that the Ms. T-less mutant exhibits thymic hypercellularity despite a lack of positive selection.

Splenic B cell maturation appears altered in Ms. T-less mice. Splenocytes from mutant and wt mice were analyzed by flow cytometry using antibodies against IgM and IgD to follow B cell (B220+ cell) maturation. The results indicate that mutant mice have a possibly elevated representation of IgM$^+$ IgD$^{dull/-}$transitional type 1 (T1) cells, a decreased percentage of IgM$^+$IgD$^+$ transitional type 2 (T2) cells, yet a normal percentage of IgM$^{dull}$IgD$^+$ mature cells.

Example 3

Normal Ca$^{2+}$ Responses in Ms. T-less Thymocytes

ITPKB converts IP3 to IP4. IP3 is a well characterized second messenger involved in calcium signaling. TCR ligation leads to activation of phospholipase Cγ(PLCγ), which hydrolyzes phosphatidylinositol (4,5) bisphosphate (PIP2) to diacylglycerol (DAG) and IP3. The augmentation of intracellular IP3 levels triggers the release of Ca$^{2+}$ from internal stores via IP3 receptors. In Jurkat cells, ITPK activity and IP4 production are elevated upon TCR stimulation. Thus, ITPKB could serve to limit TCR induced Ca$^{2+}$ mobilization via conversion of IP3 to IP4. However, it has also been postulated that IP4 can potentiate IP3 signaling via specific inhibition of a 5'-phosphatase that hydrolyzes IP3 to inositol (1,4) bisphosphate (IP2). Thus, formation of IP4 could also affect Ca$^{2+}$ mobilization positively. We therefore investigated whether defects in Ca$^{2+}$ signaling might underlie the developmental defect in Ms. T-less thymocytes.

The results indicate that DP thymocytes from Ms. T-less mice exhibit a normal calcium flux in response to CD3 crosslinking, as well as to ionomycin and thapsigargin stimulation. Thymocytes from mutant and wt mice labeled with Fura Red and Fluo-4 were either treated with biotinylated anti-CD3 antibody crosslinked with streptavidin, or stimulated with ionomycin or thapsigargin. The calcium flux of DP cells was determined as the ratio of the two calcium dyes measured over time after stimulation. The data suggest that Ms. T-less thymocytes have no major defects in internal Ca2+ release or external Ca$^{2+}$ influx.

We next investigated the Ca$^{2+}$ responses of individual cells to TCR stimulation. Thymocytes undergoing positive selection display dramatic oscillations of intracellular Ca$^{2+}$ levels which have a periodicity on the order of seconds. Cells which do not receive signals for positive selection do not show the same magnitude of oscillations at the single cell level. In HeLa cells, ITPK activity and IP4 have been implicated in the modulation of histamine-induced Ca$^{2+}$ oscillations. Surprisingly, single cell imaging of Fura-2 labeled thymocytes did not reveal significant differences in magnitude or periodicity of TCR-induced Ca$^{2+}$ oscillations between wt and mutant mice. Taken together, these data suggest that defects in Ca$^{2+}$ signaling are unlikely to underlie the profound defect in T cell development observed in Ms. T-less mice.

Example 4

The Defect in T cell Development is Inherent to the T cells

The DP block of T cell development in Ms. T-less mice is reminiscent of the phenotype seen in mice lacking both MHC I and MHC II proteins. However, we found no major differences in MHC protein expression between wt and mutant animals. This does not preclude the possibility that an unknown ligand which is necessary for differentiation into mature CD4$^+$ or CD8$^+$ T cells could be presented on the thymic epithelium and lacking in Ms. T-less mice. To address this issue, we performed bone marrow reconstitution experiments into lethally irradiated, B6.SJL hosts. The irradiation depletes the hosts of their complement of hematopoietic cells and precursors, yet keeps the thymic epithelium intact. We observed a profound block of T cell development at the DP stage in hosts reconstituted with Ms. T-less bone marrow. In addition, no T cells were present in the periphery, although B cells reconstituted efficiently. Bone marrow from wt mice exhibited normal T cell development in the host thymus. Wild type bone marrow reconstitution into lethally irradiated Ms. T-less hosts exhibited normal T cell development in the thymus. These findings indicate that the developmental block in T cell maturation is intrinsic to the developing thymocytes and does not depend upon ligands on, or signals from the thymic epithelium.

Example 5

Ms. T-less Mutant Mice Harbor a Nonsense Mutation in the IP3KB Gene

To determine the genetic lesion underlying the Ms. T-less phenotype, mutant mice on a C57BL/6 background were crossed to wt 129SvJ mice. SNP genotyping of multiple phenotypically mutant or wt F2 offspring revealed a perfect phenotype-genotype correlation for a 2 MB interval distal on chromosome 1. Analysis of this region did not reveal any obvious candidate genes known to be involved in thymic development. Thus, we examined the expression status of most known or predicted genes in the region using the GNF Gene Expression Atlas (http://expression.gnf.org). We found that the Itpkb transcript accumulates in both murine and human lymphoid tissues, especially the thymus.

Sequencing of this candidate gene revealed a T to A transversion at position 596 of the transcript, changing the codon encoding cysteine 199 to a stop. The mutant transcript encodes an N-terminally truncated ITPKB protein lacking most of its structure, including domains that are involved in targeting and regulation, as well as the catalytic domain.

Immunoblot analyses of lysates from sorted CD4+ CD8+ DP cells, or of immunoprecipitates from whole thymocyte extracts, revealed that Ms. T-less thymocytes lack full length ITPKB protein. Expression of Itpkb RNA, however, is quite abundant in sorted mutant DP thymocytes. In agreement with these data, extracts from Ms. T-less thymocytes showed an approximately 50% reduction of ITPK activity compared to wt extracts. This residual activity could reflect low level thymic expression of other ITPK isoforms. Our data suggest that lack of full length ITPKB protein expression and concomitant reduction of ITPK activity in thymocytes underlie the defect in T cell development in Ms. T-less mice.

Example 6

Defective Erk Activation in Ms. T-less Thymocytes

The lack of an overt effect on $Ca^{2+}$ responses in Ms. T-less thymocytes led us to consider other mechanisms of how IP3KB could control T cell selection. Since IP3 levels do not seem to be affected in these mice, we addressed putative mechanisms involving IP4. The protein $GAP1^{IP4BP}$ has been shown to bind IP4 with high affinity and specificity in vitro. $GAP1^{IP4BP}$ is a GTPase activating protein (GAP) that stimulates the small GTPase Ras to convert GTP to GDP, rendering Ras inactive. Several studies have demonstrated essential roles for the Ras pathway in T cell development. It has been shown that functional inactivation of the Ras activator Ras-GRP, Ras, or components of the MAP-kinase pathway downstream of Ras, all affect maturation of DP thymocytes and positive selection. Therefore, $GAP1^{IP4BP}$ could be an important component which connects IP3KB mediated IP4 production to Ras activation in T cell development.

To address activation of the Ras pathway in Ms. T-less thymocytes, cells were stimulated with either a suboptimal TCR signal using a CD3 alone or with a maximal TCR signal using a combination of αCD3 and αCD4 antibodies. Ras activation leads to the activation and phosphorylation of the MAP kinases Erk1 and Erk2. Via immunoblot analysis, we found a significant impairment of Erk1 and Erk2 activation in response to suboptimal (αCD3 alone) stimulation in Ms. T-less thymocytes. Optimal stimulation conditions (αCD3 and αCD4) or stimulation with the diacylglycerol (DAG) analog phorbol 12-myristate 13-acetate (PMA), which can localize RasGRP1 to the plasma membrane to allow for Ras activation, elicited normal levels of Erk1 and Erk2 activation.

These data demonstrate that Ms. T-less thymocytes are unable to efficiently activate Erk1 and Erk2 under moderate stimulation conditions. Thus, the block during positive selection in Ms. T-less thymocytes may reflect critical roles for IP3KB and its product IP4 as regulators of TCR induced Ras activation.

It is understood that the examples and embodiments described herein are for illustrative purposes only and that various modifications or changes in light thereof will be suggested to persons skilled in the art and are to be included within the spirit and purview of this application and scope of the appended claims. Although any methods and materials similar or equivalent to those described herein can be used in the practice or testing of the present invention, the preferred methods and materials are described.

All publications, GenBank sequences, patents and patent applications cited herein are hereby expressly incorporated by reference in their entirety and for all purposes as if each is individually so denoted.

We claim:

1. A method for identifying an agent that inhibits T lymphocyte development, the method comprising:
   (a) assaying inositol 1,4,5-trisphosphate 3-kinase B (IP3KB) kinase activity in the presence of a test agent, or assaying the level of IP3KB polypeptide or IP3KB gene expression in a cell in the presence of a test agent;
   (b) identifying one or more agents that inhibit IP3KB kinase activity, or that inhibit the level of IP3KB polypeptide or IP3KB gene expression in the cell; and
   (c) testing said one or more agents for ability to inhibit CD4+CD8+ T cell development into CD4+ or CD8+ T cells.

2. The method of claim 1, wherein said one or more agents identified in step (b) inhibit IP3KB kinase activity.

3. The method of claim 2, wherein the kinase activity is to catalyze conversion of inositol 1,4,5-triphosphate (IP3) to inositol 1,3,4,5-tetrakisphosphate (IP4).

4. The method of claim 1, wherein the IP3KB has the amino acid sequence of SEQ ID NO: 1.

5. The method of claim 1, wherein the IP3KB is encoded by a polynucleotide having the nucleotide sequence of SEQ ID NO: 2, 3, or 4.

6. The method of claim 1, wherein said one or more agents identified in step (b) inhibit the level of IP3KB polypeptide in the cell.

7. The method of claim 6, wherein the cell is selected from the group consisting of thymus cell, CD4+ CD8+ T cell, CD4+ T cell, CD8+ T cell, and NK cell.

8. The method of claim 6, wherein said one or more agents identified in step (b) inhibit the level of IP3KB gene expression in the cell.

9. The method of claim 1, wherein step c) comprises testing said one or more agents for ability to inhibit T lymphocyte development in vivo or in vitro.

10. The method of claim 9, wherein step c) comprises testing said one or more agents for ability to inhibit T lymphocyte development in a non-human animal harboring IP3KB.

11. The method of claim 10, wherein said non-human animal is a transgenic mouse.

* * * * *

SEQUENCE LISTING

<160> NUMBER OF SEQ ID NOS: 4

<210> SEQ ID NO 1
<211> LENGTH: 1192
<212> TYPE: PRT
<213> ORGANISM: Mus musculus

<400> SEQUENCE: 1

```
Thr Pro Pro Pro Cys Leu Arg Glu Phe Leu Phe Ser Leu Cys Leu His
1               5                   10                  15

Ser Arg Glu Ile Val Tyr Gly Ala Trp Gly Gly Gly Arg Ala Arg Asp
            20                  25                  30

Phe Ala Leu Cys Pro Pro Arg Pro Cys Cys Ser Ile Ser Ala Gln
        35                  40                  45

Ser Tyr Gly Arg Arg Ala Ser Gly Thr Lys Pro Arg Ala Ala Gly Gly
    50                  55                  60

Gly Gly Ala Gly Gly Ala Gly Arg Arg Ala Ala Ala Gly Gly
65                  70                  75                  80

Pro Cys Thr Met Ala Val Tyr Cys Tyr Ala Leu Asn Ser Leu Val Ile
                85                  90                  95

Met Asn Ser Thr Asn Glu Leu Lys Ser Gly Gly Pro Arg Pro Ser Gly
                100                 105                 110

Ser Glu Thr Pro Gln Pro Ser Gly Arg Ala Ala Leu Ser Pro Gly Ser
```

-continued

```
                115                 120                 125
Val Phe Ser Pro Gly Arg Gly Ala Ser Phe Leu Phe Pro Pro Ala Glu
    130                 135                 140

Ser Leu Ser Leu Glu Glu Pro Gly Ser Pro Gly Gly Trp Arg Ser Gly
145                 150                 155                 160

Arg Arg Arg Leu Asn Ser Ser Gly Ser Gly Gly Ser Ser Ser
                165                 170                 175

Ser Asn Ser Ser Ser Ser Gly Val Gly Ser Pro Ser Trp Ala Gly
            180                 185                 190

Arg Leu Arg Gly Asp Ala Gln Gln Val Ala Ala Arg Ile Leu Ser
        195                 200                 205

Pro Pro Gly Pro Glu Glu Ala Gln Arg Lys Leu Arg Ile Leu Gln Arg
    210                 215                 220

Glu Leu Gln Asn Val Gln Val Asn Gln Lys Val Gly Met Phe Glu Ala
225                 230                 235                 240

Gln Ile Gln Ala Gln Ser Ser Ala Ile Gln Ala Pro Arg Ser Pro Arg
                245                 250                 255

Leu Gly Arg Ala Arg Ser Pro Ser Pro Cys Pro Phe Arg Ser Ser Ser
            260                 265                 270

Gln Pro Pro Glu Arg Val Leu Ala Pro Cys Ser Pro Ser Glu Glu Arg
        275                 280                 285

Arg Thr Lys Ser Trp Gly Glu Gln Cys Thr Glu Thr Pro Asp Thr Asn
    290                 295                 300

Ser Gly Arg Arg Ser Arg Leu Ser Thr His Pro Ser Lys Asp Lys Glu
305                 310                 315                 320

Gly Val Ala Pro Leu Leu Gly Pro Ala Ser Pro Thr Arg Leu Gly Thr
                325                 330                 335

Gln Ser Pro Ser Thr Ser Val Arg Met Glu Arg Gly Thr Pro Ala Ser
            340                 345                 350

Pro Arg Cys Gly Ser Pro Thr Pro Met Glu Thr Asp Lys Arg Val Ala
        355                 360                 365

Pro Ser Leu Glu Arg Phe Gly Thr Ser Leu Thr Leu Ala Thr Lys Val
    370                 375                 380

Ala Ala Ser Ala Ala Ser Ala Gly Pro His Pro Gly His Asp Ser Ala
385                 390                 395                 400

Leu Met Glu Thr Gly Cys Glu Leu Gly Gly Met Arg Pro Trp Glu Ala
                405                 410                 415

Gln Met Glu Arg Arg Gly Gln Phe Leu Gly Lys Glu Thr Gly Ser Thr
            420                 425                 430

Pro Glu Pro Val Arg Thr His Met Arg Glu Pro Pro Gly Arg Val Gly
        435                 440                 445

Arg Gly Ile His Ser Val Gly Gly Gln Gly Ser Trp Thr Pro Glu Val
    450                 455                 460

Ile Lys Arg Pro Glu Glu Arg Ala Val Thr Ala Gln Ser Ser Glu Pro
465                 470                 475                 480

Ser Glu Asp Pro Arg Trp Ser Arg Leu Pro Val Asp Leu Asp Ser Val
                485                 490                 495

Gly Pro Glu Lys Gly Gly Asn Arg Ile Pro Gly Met Arg Gly Pro Gln
            500                 505                 510

Gln Thr Leu Asp Ser Glu Arg Glu Gly Ser Pro Ala Leu Gly Leu Leu
        515                 520                 525

Gly Gly Ser Gln Ala Ala Gln Pro Gly Ala Arg Gly Val Glu Glu Asp
    530                 535                 540
```

-continued

```
Val His Tyr Gly Arg Met Leu Glu Pro Leu Pro Pro Gly Glu Val Thr
545                 550                 555                 560

Thr Lys Leu Lys Glu Pro Gln Cys Leu Pro Gly Asp Arg Met Gly Met
                565                 570                 575

Gln Pro Glu Ser Ser Ile Val Trp Pro Ser Ala Leu Glu Glu Ala Pro
            580                 585                 590

Leu Ile Trp Thr Arg Asp Thr Gly Val Gln Ser Lys Gly Thr Trp Gly
        595                 600                 605

Ser Gln Leu Pro Asp Gly Asp Ala His Pro Ser Cys Gln Glu Met Pro
    610                 615                 620

Pro Asp Gln Lys Asp Lys Ala Ser Leu Lys Glu Ala Cys Ser Pro Ser
625                 630                 635                 640

Asn Ile Pro Ala Ile Pro Ala Val Ile Ile Thr Asp Met Gly Ala Gln
                645                 650                 655

Glu Asp Gly Gly Leu Glu Glu Ile Gln Gly Ser Pro Arg Gly Pro Leu
            660                 665                 670

Pro Leu Arg Lys Leu Ser Ser Ser Ala Ser Ser Thr Gly Phe Ser
        675                 680                 685

Ser Ser Tyr Asp Asp Ser Glu Glu Asp Ile Ser Ser Asp Pro Glu Arg
    690                 695                 700

Thr Leu Asp Pro Asn Ser Ala Phe Leu His Thr Leu Asp Gln Gln Lys
705                 710                 715                 720

Pro Arg Val Ser Lys Ser Trp Arg Lys Ile Lys Asn Met Val Gln Trp
                725                 730                 735

Ser Pro Phe Val Met Ser Phe Lys Lys Tyr Pro Trp Ile Gln Leu
            740                 745                 750

Ala Gly His Ala Gly Ser Phe Lys Ala Ala Asn Gly Arg Ile Leu
        755                 760                 765

Lys Lys His Cys Glu Ser Glu Gln Arg Cys Leu Asp Arg Leu Met Ala
770                 775                 780

Asp Val Leu Arg Pro Phe Val Pro Ala Tyr His Gly Asp Val Val Lys
785                 790                 795                 800

Asp Gly Glu Arg Tyr Asn Gln Met Asp Asp Leu Leu Ala Asp Phe Asp
                805                 810                 815

Ser Pro Cys Val Met Asp Cys Lys Met Gly Val Arg Thr Tyr Leu Glu
            820                 825                 830

Glu Glu Leu Thr Lys Ala Arg Lys Lys Pro Ser Leu Arg Lys Asp Met
        835                 840                 845

Tyr Gln Lys Met Val Glu Val Asp Pro Glu Ala Pro Thr Glu Glu Glu
    850                 855                 860

Lys Ala Gln Arg Ala Val Thr Lys Pro Arg Tyr Met Gln Trp Arg Glu
865                 870                 875                 880

Thr Ile Ser Ser Thr Ala Thr Leu Gly Phe Arg Ile Glu Gly Ile Lys
                885                 890                 895

Lys Glu Asp Gly Ser Val Asn Arg Asp Phe Lys Lys Thr Lys Thr Arg
            900                 905                 910

Glu Gln Val Thr Glu Ala Phe Arg Glu Phe Thr Lys Gly Asn Gln Asn
        915                 920                 925

Ile Leu Ile Ala Tyr Arg Asp Arg Leu Lys Ala Ile Arg Ala Thr Leu
    930                 935                 940

Glu Ile Ser Pro Phe Phe Lys Cys His Glu Val Ile Gly Ser Ser Leu
945                 950                 955                 960
```

-continued

```
Leu Phe Ile His Asp Lys Lys Glu Gln Ala Lys Val Trp Met Ile Asp
            965                 970                 975

Phe Gly Lys Thr Thr Pro Leu Pro Glu Gly Gln Thr Leu Gln His Asp
            980                 985                 990

Val Pro Trp Gln Glu Gly Asn Arg  Glu Asp Gly Tyr Leu  Ser Gly Leu
            995                 1000                1005

Asp Asn  Leu Ile Asp Ile  Leu  Thr Glu Met Ser Gln  Gly Ser Pro
            1010                1015                1020

Leu Thr  Gly His Arg His Arg  Ala Pro Cys His  Phe  Ala Arg His
            1025                1030                1035

Leu Cys  Leu Ser Pro Leu Ser   Ser Pro Asn Ser Ser   Phe Ser Cys
            1040                1045                1050

Leu Ser  Ala Tyr Leu Glu Gln   Ser Leu Pro Ser Ala   Leu Gln Asp
            1055                1060                1065

Thr Leu  Glu Lys Lys Lys Arg  Phe Phe Phe Ser Arg   Ser Leu Leu
            1070                1075                1080

Pro Arg  Pro Pro Thr Gly Leu  Gly Gly Gly Val Ser   His Ala Leu
            1085                1090                1095

Ile Glu  Pro Pro Ser Arg Arg   Glu Leu His Lys Ala   Arg Pro His
            1100                1105                1110

Ile Leu  Leu His Ser Glu Ser  Ala Arg Val Gln Lys   Ala Val Ser
            1115                1120                1125

Leu Val  Ala Ser Leu Glu Arg  Leu Ser Leu Pro Leu   Gly Asp Thr
            1130                1135                1140

Ala Pro  Leu Pro Glu Asn Ser  Gly Pro His Trp Leu   Pro Val Gly
            1145                1150                1155

Ala Leu  Leu Pro Pro Ser Gly  Cys His Gln Ala Gln   Ser His Leu
            1160                1165                1170

Cys Leu  Ser Pro Arg Ala Leu  Lys Pro Gly Gln Gly   Pro Asp Phe
            1175                1180                1185

Trp Glu  Leu Glu
            1190
```

<210> SEQ ID NO 2
<211> LENGTH: 2841
<212> TYPE: DNA
<213> ORGANISM: Homo sapiens

<400> SEQUENCE: 2

```
atggctgtgt actgctatgc gctcaatagc ctggtgatca tgaatagcgc caacgagatg      60
aagagcggcg gcggcccggg gcccagtggc agcgagacgc cccgccccc gaggagggca     120
gtgctgagcc ccggcagcgt tttcagcccc gggagaggcg cctctttcct cttccccca     180
gccgagtcgc tgtcccccga ggagccccgg agccccgggg gctggcggag cggccggcgc    240
aggctgaata gtagcagcgg cagtggcagc ggcagcagcg cagtagcgt gagcagccca     300
agttgggctg gtcgcctgcg aggggaccgg cagcaggtgg tggcagccgg tacctctcc     360
ccgccagggc cggaggaggc caagaggaag ctgcggatct tgcagcgcga gttgcagaac     420
gtgcaggtga accagaaagt gggcatgttt gaggcgcaca tccaggcaca gagctccgcc     480
attcaagcgc cccgcagccc cgtttggcag gggctcgct cgcctccccc gtgccccttc     540
cgcagcagca gtcagccccc tggaagggtc ctggttcagg gcgcccggag cgaggaacgg     600
aggacaaagt cctggggga gcaatgtcca gagacttcag gaaccgactc cgggaggaaa     660
ggaggcccca gcctatgctc ctcgcaggtg aagaaaggaa tgccacctct tcccggccgg     720
```

| | |
|---|---|
| gctgcccta caggatcaga ggctcagggt ccatccgctt ttgtaaggat ggagaagggt | 780 |
| atccctgcca gtccccgctg tggctcaccc acagctatgg aaattgacaa aagggctct | 840 |
| cctaccccgg gaactcggag ctgcctagct ccctcattgg ggctgttcgg agctagctta | 900 |
| acgatggcca cggaagtggc agcgagagtt acatccactg gccacaccg tccacaggat | 960 |
| cttgccctca ctgagccgtc tgggagagcc cgtgagcttg aggacctgca gcccccagag | 1020 |
| gccctggtgg agaggcaggg gcagtttctg ggcagtgaga caagcccagc cccagaaagg | 1080 |
| ggcgggcccc gcgatggaga acccctggg aagatgggga aaggatatct gccctgtggc | 1140 |
| atgccgggct ctggggagcc tgaagtgggc aaaaggccag aggagacgac tgtgagcgtg | 1200 |
| caaagcgcag agtcctctga tgccctgagc tggtccaggc tgcccagggc cctggcctcc | 1260 |
| gtaggccctg aggaggcccg aagtgggggcc ccgtgggcg ggggcgttg gcagctctcc | 1320 |
| gacagagtgg agggagggtc cccaacgctg ggcttgcttg ggggcagccc ctcagcacag | 1380 |
| ccggggaccg ggaatgtgga ggcgggaatt ccttctggca gaatgctgga gcctttgccc | 1440 |
| tgttgggacg ctgcgaaaga tctgaaagaa cctcagtgcc ctcctgggga cagggtgggt | 1500 |
| gtgcagcctg ggaactccag ggtttggcag ggcaccatgg agaaagccgg tttggcttgg | 1560 |
| acgcgtggca caggggtgca atcagagggg acttgggaaa gccagcggca ggacagtgat | 1620 |
| gccctcccaa gtccggagct gctaccccaa gatcaggaca agcctttcct gaggaaggcc | 1680 |
| tgcagcccca gcaacatacc tgctgtcatc attacagaca tgggcaccca ggaggatggg | 1740 |
| gccttggagg agacgcaggg aagccctcgg ggcaacctgc ccctgaggaa actgtcctct | 1800 |
| tcctcggcct cctccacggg cttctcctca tcctacgaag actcagagga ggacatctcc | 1860 |
| agtgaccctg agcgcaccct ggaccccaac tcagctttcc tgcatacct ggaccagcag | 1920 |
| aaacctagag tgagcaaatc atggaggaag ataaaaaaca tggtgcactg gtctccttc | 1980 |
| gtcatgtcct tcaagaagaa gtaccctggg atccagctgg caggacacgc agggagttc | 2040 |
| aaggcagctg ccaatggcag gatcctgaag aagcactgtg agtcagagca gcgctgcctg | 2100 |
| gaccggctga tggtggatgt gctgaggccc ttcgtacctg cctaccatgg ggatgtggtg | 2160 |
| aaggacgggg agcgctacaa ccagatggac gacctgctgg ccgacttcga ctcgccctgt | 2220 |
| gtgatggact gcaagatggg aatcaggacc tacctgagg aggagctcac gaaggcccgg | 2280 |
| aagaagccca gcctgcggaa ggacatgtac cagaagatga tcgaggtgga ccccgaggcc | 2340 |
| cccaccgagg aggaaaaagc acagcgggct gtgaccaagc cacggtacat gcagtggcgg | 2400 |
| gagaccatca gctccacggc caccctgggg ttcaggatcg agggaatcaa aaagaagac | 2460 |
| ggcaccgtga accgggactt caagaagacc aaaacgaggg agcaggtcac cgaggccttc | 2520 |
| agagagttca ctaaaggaaa ccataacatc ctgatcgcct atcgggaccg gctgaaggcc | 2580 |
| attcgaacca ctctagaagt ttctcccttc ttcaagtgcc acgaggtcat tggcagctcc | 2640 |
| ctcctcttca tccacgacaa gaaggaacag gccaaagtgt ggatgatcga ctttgggaaa | 2700 |
| accacgcccc tgcctgaggg ccagaccctg cagcatgacg tccctggca ggaggggaac | 2760 |
| cgggaggatg gctacctctc ggggctcaat aacctcgtcg acatcctgac cgagatgtcc | 2820 |
| caggatgccc cactcgcctg a | 2841 |

<210> SEQ ID NO 3
<211> LENGTH: 2805
<212> TYPE: DNA
<213> ORGANISM: Rattus norvegicus

```
<400> SEQUENCE: 3
atggctgtgt actgctatgc cctcaatagc ctggtgatca tgaacagcac caacgagctg       60
aagagtggca gccccctgcc cagcggcagc gaaacgcctc agccctccgg gagggccgcg      120
ctgagccccg gcagcgtctt cagccctggg agaggcgcct cctttctctt cccccagca       180
gagtcgctgt cgctggagga gcctgggagt gctggggtt ggcgcagcgg ccgacggagg       240
ctgaatagta gcagcggtag cggaggtggc agcagcagca gcaacagcag cagcagcagt      300
ggcgtgggca gtcccagttg ggctggccgc ctgcgagggg acgcgcagca ggtggtggcg      360
acccgcatcc tctccccacc tgggccgag gaggcccaga ggaagctgag gattctgcag       420
cgcgaattgc aaaatgtgca ggtgaaccag aaagtgggca tgttcgaggc gcaaatccag      480
gcacagacct ctgctattca agcgccccga agcccgcgtt tgggtagggc tcgttcgccc      540
tccccgtgtc ccttccgaag cagcagccag cctcctgaaa gggtcttggc tccatgttcc      600
ccaagtgagg aacggagaac aaagtcctgg ggagaacaat gtacagagac cccagatgcc      660
aactccagga ggagaagcag actcagcaca caccccctcga aggacaagga gggagtggcc      720
cctcttttag gcccagccag cccgaccagg ttagggactc agagtccatc tacttcagtg      780
agaatggaaa gaggttcccc ggccagtccc cgctgtggct cacccacacc catggaaatt      840
gacaagagga ctgctccctc actggagcac tttgggacta gcttaacgtt ggccactaaa      900
gtggcagctt cggccgcatc cgctggacca caccctggac atgattctgt tctcatggag      960
gcagactgtg agctagggc catgcgcccc tgggaggccc acctggagag acggggggcag     1020
tttctgggca gggagaccgg ctcagcccca gagcctatcc ggacccacat tagagaaccc     1080
cctggaaggg tggaaagagt tcattctgtt ggtggccagg gctcctggac acctgaagtc     1140
atcaaaagac cagaagaggg aactgtggat gcccaaagct cagagctctc agagaacccg     1200
agatggtcta gactgcctgg agacccgggt tccgtagggc ctgagaaggg aggtagtagg     1260
atcccaggaa tccgaggacc ccagcagacc ctggacagca tgagagaagg gtcttcagca     1320
ctgggcttgc ttgggggcag ccaggcagca cagccaggga gcatggatgt ggagacaggc     1380
attagttgtg gcagaatgct ggaaccctta ccacctgggg aagtaacaac aaatttgaaa     1440
gaacccagt gcctccctgg ggacaggatg gggatgcagc ctgagagttc catagtttgg     1500
cccagtgctg tggaggaagc tcccctgatc tggacgtgtg acacagggat acagttaaag     1560
gggacttgga gaagccaaga tggagatgct catcctagct gccaagagaa gtccccagac     1620
cagaaggaca aggcctgcag ccccagcaac atcccggcca tccctgcagt catcattaca     1680
gatatgggtg ctcaggagga tggagggtta gaggagatcc aaggaagccc tcggggtccc     1740
ctgcctctga ggaagctgtc gtcctcctca gcctcctcca ctggcttctc ctcttcctat     1800
gaggactcgg aggaggacat ctccagtgac cctgagcgca ctctggaccc caactcagcc     1860
tttttgcata ccttggacca gcagaagccc agagtgagca agtcatggag gaagataaag     1920
aacatggtgc agtggtcccc ctttgtcatg tccttcaaga gaagtaccc ctggatccag      1980
ctggcaggac atgcagggag cttcaaggca gctgcgaatg ccgtatcct taagaagcat      2040
tgtgagtctg aacagcgatg cctggaccgg ttaatggcgg atgtgctgag gcccttcgtg     2100
ccagcctacc atggcgacgt ggtgaaggac ggggaacgct acaaccagat ggacgacctg     2160
ctggctgact tcgattcacc ctgcgtgatg gactgcaaga tgggcatcag gacataccdg    2220
gaggaagaac tcaccaaggc ccggaagaag cctagcttgc ggaaggacat gtaccagaag     2280
atggtggagg tggaccctga ggcccccact gaagaggaga agcccagag agctgtgacc     2340
```

```
aagccacgtt atatgcagtg gcgggaaacc atcagttcca cagctacctt aggcttcagg    2400
atcgagggca tcaagaagga agatggctct gtgaaccgtg acttcaagaa gaccaaaaca    2460
agggagcagg tcactgaggc cttcagagaa ttcactaaag gaaaccagaa catcctgatt    2520
gcctaccggg accggttgaa ggccattcga gaaaccctgg aagtctctcc cttcttcaag    2580
tgccatgagg tcattggcag ctctctcctc ttcatccacg acaagaagga gcaagccaag    2640
gtgtggatga ttgactttgg gaaaaccacg ccccttccgg aaggccagac cctacaacac    2700
gatgtcccct ggcaggaggg gaaccgggag gatggctacc tctcagggct gaacaacctc    2760
atcgacatcc tgacagaaat gtcccagggc agcccactca cctga                   2805

<210> SEQ ID NO 4
<211> LENGTH: 3608
<212> TYPE: DNA
<213> ORGANISM: Mus musculus

<400> SEQUENCE: 4
caccccaccc ccttgatgcc ttcgggaatt ctgacttttc tccttgtgtc tccacagccg      60
cgaaatcgtt tatggagctt ggggcggggg ccgagcccgc gattttgccc tgtgcccgcc     120
gcctaggcca tgctgctcca tcagcgcgca gagctacggc cgccgggcct ccggggactaa    180 gccgagagcc gcgggaggag gaggcgccgg cgctggagcg ggacggagag ccgcggcggc    240
gggcggaccc tgtactatgg ctgtgtactg ctatgccctc aatagcctgg tgatcatgaa    300
cagcaccaac gagctcaaga gtggcggccc ccggcccagc ggcagcgaga cgccccagcc    360
ctccgggagg gccgcgctga gtcccggcag cgtcttcagc cctgggagag gcgcttcctt    420
tctcttcccc ccagcagagt cgctgtccct ggaggagccc gggagtcctg ggggctggcg    480
cagcggccgg cgcaggctga atagtagcag cggtagcgga ggtggcagca gcagcagcaa    540
cagcagcagc agcagtggcg tgggcagtcc cagtttgggct ggccgcctgc gaggggacgc   600
gcagcaggtg gtggcggccc gcatcctctc cccacctggg ccagaggagg cccagaggaa    660
gctgcggatt ctgcagcgcg agttgcaaaa tgtgcaggtg aaccagaaag tgggcatgtt    720
cgaggcgcaa atccaggcac agagctctgc cattcaagcg ccccgaagcc gcgtttggg     780 tagggctcgt tcgccctccc cgtgtccctt ccgaagtagc agccagcccc cgaaagggt     840 cttggctccg tgttctccaa gtgaggaacg cagaacaaag tcctggggag aacaatgtac    900
agaaacccca gataccaact ctggaaggag aagcagactc agcacacacc cctcgaagga    960
caaggaggga gtggccccctc ttttaggccc agccagcccg accaggttag ggactcagag   1020
tccatctact tccgtgagaa tggaaagagg taccccggcc agtccccgct gtggctcacc    1080
cacacccatg gaaactgaca agagggttgc tccctcactg gagcgctttg gaactagctt    1140
aacgttggct actaaagtgg cagcttcagc cgcatccgct ggaccacacc ctggacatga    1200
ttctgccctc atggagacag gctgtgagct cgggggcatg cgcccctggg aggcccagat    1260
ggagagacgg gggcagtttc tgggcaagga gaccggctca accccagagc ctgtccggac    1320
ccacatgaga gaaccccctg aagggtggg aagaggaatt cattctgttg gtgggcaggg    1380
ctcctggaca cctgaagtca tcaaaagacc agaagagagg gctgtgactg cccaaagctc    1440
agagccctca gaggaccccca gatggtctag actgcctgta gacctggatt ccgtaggacc   1500
tgagaaggga ggaaatagga tcccagggat gcgagggccc cagcagaccc tggacagtga    1560
gagagaaggc tctccagcac tgggcttgct tgggggcagc caggcagcac agccagggc    1620
```

```
tagggggtgtg gaggaagacg ttcattatgg ccgaatgctg gaacctttac cacctgggga    1680
agtaacaaca aaattgaaag aacccccagtg cctccctggg gacaggatgg gaatgcagcc   1740
tgagagttcc atagtttggc ccagtgcctt ggaggaagct cccctgatct ggacacgtga   1800
cacgggggta cagtcgaagg ggacttgggg aagccagctg ccagacggag atgctcaccc   1860
tagctgccaa gagatgcccc cagaccagaa ggacaaggcc tccttaaaag aggcctgcag   1920
ccccagcaac atcccagcca tccctgcagt catcattaca gatatgggtg ctcaggagga   1980
tggagggcta gaggagatcc aaggaagccc tcggggtccc ctgcctctga ggaagctgtc   2040
ctcctcctca gcctcctcca ctggcttctc ctcttcttac gatgactcgg aggaggacat   2100
ctccagtgac cctgagcgca cgctggaccc caactcagcc tttttgcata ccctggacca   2160
gcagaagccc agagtgagca agtcatggag aaagataaag aacatggtgc agtggtcccc   2220
ctttgtcatg tccttcaaga agaagtaccc ctggatccag ctggcaggac atgcagggag   2280
cttcaaggca gctgcaaatg gccgcatcct taagaagcac tgtgagtctg agcagcgctg   2340
cctggaccgg ttaatggcgg atgtgctgag acccttcgtg ccagcctacc atggggacgt   2400
ggtgaaggat ggggaacgct acaaccagat ggacgacctg ctggctgact tcgattcgcc   2460
ctgcgtgatg gactgcaaga tgggtgtcag gacatacctg gaggaagaac tcaccaaggc   2520
ccggaagaag cctagcttgc ggaaggacat gtaccagaag atggtcgagg tggaccctga   2580
ggcccccact gaagaggaga agcccagcg agctgtgacc aagccacgtt acatgcagtg   2640
gcgggaaacc atcagttcga cagccaccct aggcttcagg atcgaaggca tcaagaagga   2700
agatggctct gtgaaccgtg acttcaagaa gaccaaaaca agggagcagg tcaccgaggc   2760
tttcagagaa ttcactaagg gaaaccagaa catcttgatc gcctaccggg accggctgaa   2820
ggccattcga gcgaccctgg aaatctctcc cttcttcaag tgccacgagg tcattggcag   2880
ctctctcctc ttcatccatg acaagaagga gcaagccaag gtgtggatga ttgactttgg   2940
gaaaaccacg cccccttccgg aaggccagac cctacaacac gacgtcccct ggcaggaggg   3000
gaaccgggag gatggctacc tctcagggct ggacaacctc atcgacatcc tgacggaaat   3060
gtcccagggc agcccactca cctgaggcca ccgccaccgt gcatagccgt gccactttgc   3120
ccgccacctc tgcctgtcgc ctctctcctc ccctaattct tcctttttcct gtctgagcgc   3180
ctacctagaa cagagcctcc catctgcact acaggacact ttggagaaaa aaaagagatt   3240
ttttttttct agatctttac ttccccggcc tcctacatag gggcttggag gtggcgtttc   3300
tcatgctctc taaatagaac caccttctcg aagagaatta cacaaagcta ggccccacat   3360
cctgttacac tcagagtcgg cacgggtcca gaaggccgtg tgatccctgg ttgcctaaag   3420
tcttgagaga ttaagcctcc ctctgggaga cactgccccc ctcccagaaa attctggccc   3480
acactggcta ccagtagggg ccttgctgcc ccctagtggc taatgccatc agtaagcaca   3540
gtcccatttg tgcctctcac cacgggccct gaagccagga cagggacctg atttctggga   3600
gttggaaa                                                              3608
```